United States Patent
Boyden et al.

(10) Patent No.: US 12,077,822 B2
(45) Date of Patent: *Sep. 3, 2024

(54) METHODS FOR DETERMINING CARRIER STATUS

(71) Applicant: Molecular Loop Biosciences, Inc., Cambridge, MA (US)

(72) Inventors: Eric D. Boyden, Cambridge, MA (US); Gregory Porreca, Cambridge, MA (US); Mark Umbarger, Brookline, MA (US)

(73) Assignee: Molecular Loop Biosciences, Inc., Cambridge, MA (US)

(*) Notice: Subject to any disclaimer, the term of this patent is extended or adjusted under 35 U.S.C. 154(b) by 660 days.

This patent is subject to a terminal disclaimer.

(21) Appl. No.: 17/104,906

(22) Filed: Nov. 25, 2020

(65) Prior Publication Data

US 2021/0277472 A1   Sep. 9, 2021

Related U.S. Application Data

(63) Continuation of application No. 14/057,673, filed on Oct. 18, 2013, now Pat. No. 10,851,414.

(51) Int. Cl.
*C12Q 1/6883* (2018.01)
*C12Q 1/6827* (2018.01)
*C12Q 1/6874* (2018.01)

(52) U.S. Cl.
CPC ......... *C12Q 1/6883* (2013.01); *C12Q 1/6827* (2013.01); *C12Q 1/6874* (2013.01); *C12Q 2600/156* (2013.01); *C12Q 2600/166* (2013.01)

(58) Field of Classification Search
CPC ............ C12Q 1/6883; C12Q 2600/156; C12Q 2600/166; C12Q 2600/172
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| EP | 1 321 477 A1 | 6/2003 |
| EP | 1 564 306 A2 | 8/2005 |

(Continued)

OTHER PUBLICATIONS

Wagle, N. et al. Cancer Discovery 2(1):82 (Jan. 2012; online Nov. 7, 2011). (Year: 2011).*

(Continued)

*Primary Examiner* — Diana B Johannsen
(74) *Attorney, Agent, or Firm* — Withers Bergman LLP; Thomas C. Meyers

(57) ABSTRACT

The invention generally relates to methods for determining carrier status with respect to a condition or disease. In certain embodiments, the method involves exposing a sample to a plurality of molecular inversion probes capable of capturing DNA from at least one genomic region suspected of having an altered copy number and at least one internal control DNA known or suspected to have a stable copy number, capturing and sequencing DNA that binds to the molecular inversion probes, and determining a copy number state of the at least one genomic region based on the sequence results.

17 Claims, 2 Drawing Sheets

(56) References Cited

U.S. PATENT DOCUMENTS

| | | |
|---|---|---|
| 4,988,617 A | 1/1991 | Landegren et al. |
| 5,060,980 A | 10/1991 | Johnson et al. |
| 5,210,015 A | 5/1993 | Gelfand et al. |
| 5,234,809 A | 8/1993 | Boom et al. |
| 5,242,794 A | 9/1993 | Whiteley et al. |
| 5,348,853 A | 9/1994 | Wang et al. |
| 5,434,049 A | 7/1995 | Okano et al. |
| 5,459,307 A | 10/1995 | Klotz, Jr. |
| 5,486,686 A | 1/1996 | Zdybel, Jr. et al. |
| 5,491,224 A | 2/1996 | Bittner et al. |
| 5,494,810 A | 2/1996 | Barany et al. |
| 5,567,583 A | 10/1996 | Wang et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,869,717 A | 2/1999 | Frame et al. |
| 5,871,921 A | 2/1999 | Landegren et al. |
| 5,888,788 A | 3/1999 | De Miniac |
| 5,942,391 A | 8/1999 | Zhang et al. |
| 5,971,921 A | 10/1999 | Timbel |
| 5,993,611 A | 11/1999 | Moroney, III et al. |
| 5,994,056 A | 11/1999 | Higuchi |
| 6,020,127 A | 2/2000 | MacKenzie et al. |
| 6,033,854 A | 3/2000 | Kurnit et al. |
| 6,033,872 A | 3/2000 | Bergsma et al. |
| 6,100,099 A | 8/2000 | Gordon et al. |
| 6,138,077 A | 10/2000 | Brenner |
| 6,150,516 A | 11/2000 | Brenner et al. |
| 6,171,785 B1 | 1/2001 | Higuchi |
| 6,172,214 B1 | 1/2001 | Brenner |
| 6,172,218 B1 | 1/2001 | Brenner |
| 6,197,508 B1 | 3/2001 | Stanley |
| 6,197,574 B1 | 3/2001 | Miyamoto et al. |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vernachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,716,580 B2 | 4/2004 | Gold et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,114,027 B2 | 2/2012 | Triva |
| 8,165,821 B2 | 4/2012 | Zhang |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,738,300 B2 | 5/2014 | Porreca et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,115,387 B2 | 8/2015 | Umbarger |
| 9,228,233 B2 | 1/2016 | Kennedy et al. |
| 9,292,527 B2 | 3/2016 | Kennedy et al. |
| 9,535,920 B2 | 1/2017 | Kennedy et al. |
| 9,567,639 B2 | 2/2017 | Oliphant et al. |
| 9,677,124 B2 | 6/2017 | Umbarger |
| 10,066,259 B2 | 9/2018 | Gore et al. |
| 10,202,637 B2 | 2/2019 | Umbarger |
| 10,227,635 B2 | 3/2019 | Umbarger et al. |
| 10,604,799 B2 | 3/2020 | Porreca et al. |
| 10,683,533 B2 | 6/2020 | Umbarger et al. |
| 10,851,414 B2 * | 12/2020 | Boyden ............... C12Q 1/6827 |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0042052 A1 | 4/2002 | Nilsen et al. |
| 2002/0091666 A1 | 7/2002 | Rice et al. |
| 2002/0164629 A1 | 11/2002 | Quake et al. |

(56) References Cited

U.S. PATENT DOCUMENTS

| | | |
|---|---|---|
| 2002/0172954 A1 | 11/2002 | Mao et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1 | 9/2003 | Murphy et al. |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224384 A1 | 12/2003 | Sayood et al. |
| 2004/0029264 A1 | 2/2004 | Robbins |
| 2004/0053275 A1 | 3/2004 | Shafer |
| 2004/0106112 A1 | 6/2004 | Nilsson et al. |
| 2004/0121373 A1 | 6/2004 | Friedlander et al. |
| 2004/0142325 A1 | 7/2004 | Mintz et al. |
| 2004/0152108 A1 | 8/2004 | Keith et al. |
| 2004/0161773 A1 | 8/2004 | Rogan et al. |
| 2004/0170965 A1 | 9/2004 | Scholl et al. |
| 2004/0171051 A1 | 9/2004 | Holloway |
| 2004/0175719 A1 | 9/2004 | Christians |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1 | 8/2005 | Kowalik et al. |
| 2005/0214811 A1 | 9/2005 | Margulies et al. |
| 2005/0244879 A1 | 11/2005 | Schumm et al. |
| 2005/0250147 A1 | 11/2005 | Macevicz |
| 2005/0272065 A1 | 12/2005 | Lakey et al. |
| 2006/0008824 A1 | 1/2006 | Ronaghi et al. |
| 2006/0019304 A1 | 1/2006 | Hardenbol et al. |
| 2006/0024681 A1 | 2/2006 | Smith et al. |
| 2006/0030536 A1 | 2/2006 | Yu et al. |
| 2006/0078894 A1 | 4/2006 | Winkler et al. |
| 2006/0149047 A1 | 7/2006 | Nanduri et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0195269 A1 | 8/2006 | Yeatman et al. |
| 2006/0246500 A1 | 11/2006 | Browne |
| 2006/0263789 A1 | 11/2006 | Kincaid |
| 2006/0281098 A1 | 12/2006 | Miao et al. |
| 2006/0286577 A1 | 12/2006 | Jia |
| 2006/0292585 A1 | 12/2006 | Nautiyal et al. |
| 2006/0292611 A1 | 12/2006 | Berka et al. |
| 2007/0009925 A1 | 1/2007 | Fang et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0212704 A1 | 9/2007 | Dong et al. |
| 2007/0225487 A1 | 9/2007 | Nilsson et al. |
| 2007/0238122 A1 | 10/2007 | Allbritton et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0125324 A1 | 5/2008 | Petersdorf et al. |
| 2008/0176209 A1 | 7/2008 | Muller et al. |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0035777 A1 | 2/2009 | Kokoris et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0220955 A1 | 9/2009 | Verrant |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0076185 A1 | 3/2010 | Adey et al. |
| 2010/0086914 A1 | 4/2010 | Bentley et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0227329 A1 | 9/2010 | Cuppens |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0118145 A1* | 5/2011 | Akmaev ............... G16B 20/10 506/12 |
| 2011/0159499 A1 | 6/2011 | Hindson et al. |
| 2011/0166029 A1 | 7/2011 | Margulies et al. |
| 2011/0224105 A1 | 9/2011 | Kurn et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |

(56) References Cited

U.S. PATENT DOCUMENTS

| | | |
|---|---|---|
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0129755 A1 | 5/2013 | Song |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268206 A1 | 10/2013 | Porreca et al. |
| 2013/0268474 A1 | 10/2013 | Nizzari et al. |
| 2013/0274146 A1 | 10/2013 | Umbarger et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0337447 A1 | 12/2013 | Porreca et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0228226 A1 | 8/2014 | Yin et al. |
| 2014/0255931 A1 | 9/2014 | Porreca et al. |
| 2014/0274741 A1 | 9/2014 | Hunter et al. |
| 2014/0308667 A1 | 10/2014 | Umbarger |
| 2014/0318274 A1 | 10/2014 | Zimmerman et al. |
| 2014/0342354 A1 | 11/2014 | Evans et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0111208 A1 | 4/2015 | Umbarger et al. |
| 2015/0178445 A1 | 6/2015 | Cibulskis et al. |
| 2015/0258170 A1 | 9/2015 | McCabe et al. |
| 2015/0299767 A1 | 10/2015 | Armour et al. |
| 2015/0310163 A1 | 10/2015 | Kingsmore et al. |
| 2015/0354003 A1 | 12/2015 | Umbarger |
| 2016/0003812 A1 | 1/2016 | Porreca et al. |
| 2016/0034638 A1 | 2/2016 | Spence et al. |
| 2016/0068889 A1 | 3/2016 | Gole et al. |
| 2016/0188793 A1 | 6/2016 | Muzzey et al. |
| 2016/0210486 A1 | 7/2016 | Porreca et al. |
| 2016/0251719 A1 | 9/2016 | Umbarger |
| 2017/0044610 A1 | 2/2017 | Johnson |
| 2017/0129964 A1 | 5/2017 | Cheung |
| 2017/0183731 A1 | 6/2017 | Mann et al. |
| 2017/0275676 A1 | 9/2017 | Umbarger |
| 2018/0371533 A1 | 12/2018 | Gore et al. |
| 2019/0233881 A1 | 8/2019 | Umbarger et al. |
| 2020/0181696 A1 | 6/2020 | Porreca et al. |

FOREIGN PATENT DOCUMENTS

| | | |
|---|---|---|
| EP | 2425240 A2 | 3/2012 |
| EP | 2 437 191 A2 | 4/2012 |
| EP | 2716766 A1 | 4/2014 |
| WO | 95/011995 A1 | 5/1995 |
| WO | 1996/019586 A1 | 6/1996 |
| WO | 98/014275 A1 | 4/1998 |
| WO | 98/044151 A1 | 10/1998 |
| WO | 00/018957 A1 | 4/2000 |
| WO | 02/093453 A2 | 11/2002 |
| WO | 2004/018497 A2 | 3/2004 |
| WO | 2004/083819 A2 | 9/2004 |
| WO | 2005/003304 A2 | 1/2005 |
| WO | 2006/084132 A2 | 8/2006 |
| WO | 2007/010251 A2 | 1/2007 |
| WO | 2007/061284 A1 | 5/2007 |
| WO | 2007/107717 A1 | 9/2007 |
| WO | 2007/123744 A2 | 11/2007 |
| WO | 2007/135368 A2 | 11/2007 |
| WO | 2008067551 A2 | 6/2008 |
| WO | 2009/036525 A2 | 3/2009 |
| WO | 2009/076238 A2 | 6/2009 |
| WO | 2010/024894 A1 | 3/2010 |
| WO | 2010/115154 A1 | 10/2010 |
| WO | 2010/126614 A2 | 11/2010 |
| WO | 2011/006020 A1 | 1/2011 |
| WO | 2011066476 A1 | 6/2011 |
| WO | 2011067378 A1 | 6/2011 |
| WO | 2011/102998 A2 | 8/2011 |
| WO | 2011/155833 A2 | 12/2011 |
| WO | 2012/006291 A2 | 1/2012 |
| WO | 2012/040387 A1 | 3/2012 |
| WO | 2012/051208 A2 | 4/2012 |
| WO | 2012/087736 A1 | 6/2012 |
| WO | 2012/109500 A2 | 8/2012 |
| WO | 2012/134884 A1 | 10/2012 |
| WO | 2012/149171 A1 | 11/2012 |
| WO | 2012/170725 A2 | 12/2012 |
| WO | 2013/058907 A1 | 4/2013 |
| WO | 2013/148496 A1 | 10/2013 |
| WO | 2013/177086 A1 | 11/2013 |
| WO | 2013/191775 A2 | 12/2013 |
| WO | 2014/052909 A2 | 4/2014 |
| WO | 2014/074246 A1 | 5/2014 |
| WO | 2015/119941 A2 | 8/2015 |

OTHER PUBLICATIONS

Wagle, N. et al, Supplementary Material for Cancer Discovery 2(1):82 (online Nov. 7, 2011). (Year: 2011).*

Wang, Y. et al. Cancer Genetics 205:341 (Jul./Aug. 2012). (Year: 2012).*

Alkan, C. et al. Nature Genetics 41(10):1061 (Oct. 2009). (Year: 2009).*

Alkan, C. et al, Supplementary Information for Nature Genetics 41(10);1061 (Oct. 2009). (Year: 2009).*

O'Roak, B.J. et al. Science 338:1619 (Dec. 2012, online Nov. 2012). (Year: 2012).*

Carvill, G.L. et al. Nature Genetics 45(7):825 (Jul. 2013, online May 2013). (Year: 2013).*

Nuttle, X. et al. Nature Methods 10(9):903 (Sep. 2013, online Jul. 2013). (Year: 2013).*

O'Roak, B.J. et al. Supplementary Materials for Science 338:1619 (Dec. 2012, online Nov. 2012). (Year: 2012).*

Abravaya, 1995, Detection of point mutations with a modified ligase chain reaction (Gap-LCR), Nucleic Acids Research, 23(4): 675-682.

Adey, 2010, Rapid, low-input, low-bias construction of shotgun fragment libraries by high-density in vitro transposition, Genome Biol 11:R119, 17 pages.

Ageno, 1969, The alkaline denaturation of DNA, Biophys J 9(11):1281-1311.

Agrawal, 1990, Site-specific functionalization of oligodeoxynucleotides for non-radioactive labelling, Tetrahedron Let 31:1543-1546.

Akhras, 2007, Connector inversion probe technology: A powerful one-primer multiplex DNA amplification system for numerous scientific applications, PLoSOne 2(9):e915.

Akhras, 2007, PathogenMip Assay: a multiplex pathogen detection assay, PLOS One 2:e2230.

Alazard, 2002, Sequencing of production-scale synthetic oligonucleotides by enriching for coupling failures using matrix-assisted laser desorption/ ionization time-of-flight mass spectrometry, Anal Biochem 301:57-64.

Alazard, 2006, Sequencing oligonucleolides by enrichment of coupling failures using matrix-assisted laser desorption/ionization time-of-flight mass spectrometry, Curr Protoc Nucleic Acid Chem, Chapter 10, Unit 10:1-7.

Albert, 2007, Direct selection of human genomic loci by microarray hybridization, Nature Methods 4(11):903-5.

(56) References Cited

OTHER PUBLICATIONS

Aljanabi, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Archer, 2014, Selective and flexible depletion of problematic sequences from RNA-seq libraries at the cDNA stage, BMC Genomics 15(1):401, 9 pages.
Ball, 2009, Targeted and genome-scale strategies reveal gene-body methylation signatures in human cells, Nat Biotech 27:361-8.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.
Bau, 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carrier testing for severe childhood recessive diseases by next-generation sequencing, Sci Trans Med 3(65ra4), 15 pages.
Benner, 2001, Evolution, language and analogy in functional genomics, Trends Genet 17:414-8.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted laser desorption ionization analysis, Anal Biochem 258:31-37.
Bhangale, 2006, Automating resequencing-based detection of insertion-deletion polymorphisms, Nature Genetics 38:1457-1462.
Bickle, 1993, Biology of DNA Restriction, Microbiol Rev 57(2):434-50.
Blasczyk, 1996, Sequence analysis of the 2nd intron revealed common sequence motifs providing the means for a unique sequencing based typing protocol of the HLA-A locus, Tissue Antigens, 47:102-110.
Bonfield, 2013, Compression of FASTQ and SAM format sequencing data, PLoS One 8(3):e59190, 10 pages.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013, 2 pages.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslavsky, 2003, Sequence information can be obtained from single DNA molecules, PNAS 100:3960-4.
Brinkman, 2004, Splice Variants as Cancer Biomarkers, Clin Biochem 37:584-594.
Brison, 1982, General method for cloning amplified DNA by differential screening, Mol Cell Biol 2(5):578-587.
Brown, 1979, Chemical synthesis and cloning of a tyrosine tRNA gene, Methods Enzymol, 68:109-51.
Browne, 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the CLARITY Challenge, Genome Biol 15:R53, 8 pages.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA., 24 pages.
Carpenter, 2013, Pulling out the 1%: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.
Castellani, 2008, Consenses on the use of and interpretation of cystic fibrosis mutation analysis in clinical practice, J Cyst Fib 7:179-196.
Challis, 2012, An integrative variant analysis suite for whole exome next-generation sequencing data, BMC Informatics 13(8):1-12.
Chan, 2011, Natural and engineered nicking endonucleases-from cleavage mechanism to engineering of strand-specificity, Nucl Acids Res 39(1):1-18.
Chen, 2010, Identification of racehorse and sample contamination by novel 24-plex STR system, Forensic Sci Int: Genetics 4:158-167.
Chennagiri, 2013, A generalized scalable database model for storing and exploring genetic variations detected using sequencing data, American Society of Human Genetics 63rd Annual Meeting, Abstract, Oct. 22, 2013, 2 pages.
Chevreux, 1999, Genome sequence assembly using trace signals and additional sequence information, Proc GCB 99:45-56.
Chirgwin, 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Chou, 2010, DNA Sequence Capture and Enrichment by Microarray Followed by Next-Generation Sequencing for Targeted Resequencing: Neurofibromatosis Type 1 Gene as a Model, Clinical Chemistry, 56(1):62-72.
Ciotti, 2004, Triplet repeat prmied PCR (TP PCR) in molecular diagnostic testing for Friedrich ataxia, J Mol Diag 6(4):285-9.
Lipman, 1985, Rapid and sensitive protein similarity searches, Science 227(4693):1435-41.
Liu, 2012, Comparison of next-generation sequencing systems, J Biomed Biotech 2012:251364, 12 pages.
Llopis, 1998, Measurement of cytosolic, mitochondrial, and Golgi pH in single living cells with green fluorescent proteins, PNAS 95(12):6803-08.
Ma, 2006, Application of real-time polymerase chain reaction (RT-PCR), J Am Soc 1-15.
MacArthur, 2014, Guidelines for investigating causality of sequence variants in human disease, Nature 508:469-76.
Maddalena, 2005, Technical standards and guidelines: molecular genetic testing for ultra-rare disorders, Genet Med 7:571-83.
Malewicz, 2010, Pregel: a system for large-scale graph processing, Proc. ACM SIGMOD Int Conf Mgmt Data 135-46.
Mamanova, 2010, Target-enrichment strategies for next-generation sequencing, Nat Meth 7(2):111-118.
Margulies, 2005, Genome sequencing in micro-fabricated high-density picotiter reactors, Nature, 437:376-380.
Marras, 1999, Multiplex detection of single-nucleotide variations using molecular beacons, Genetic Analysis: Biomolecular Engineering 14:151, 6 pages.
Maxam, 1977, A new method for sequencing DNA, PNAS, 74:560-564.
May 1988, How Many Species Are There on Earth?, Science 241(4872):1441-9.
McDonnell, 2007, Antisepsis, disinfection, and sterilization: types, action, and resistance, p. 239.
McKenna, 2010, The Genome Analysis Toolkit: A MapReduce framework for analyzing next-generation DNA sequencing data, Genome Research 20:1297-1303.
Messiaen, 1999, Exon 10b of the NF1 gene represents a mutational hotspot and harbors a recurrent missense mutation Y489C associated with aberrant splicing, Genetics in Medicine, 1(6):248-253.
Meyer, 2007, Targeted high-throughput sequencing of tagged nucleic acid samples, Nucleic Acids Research 35(15):e97, 5 pages.
Meyer, 2008, Parallel tagged sequencing on the 454 platform, Nat Protocol 3(2):267-278.

(56) References Cited

OTHER PUBLICATIONS

Meyer, 2008, Parallel tagged sequencing on the 454 platform, Nature Protocols, 3(2):267-278.
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Mills, 2010, Mapping copy number variation by population-scale genome sequencing, Nature 470(7332):59-65.
Miner, 2004, Molecular barcodes detect redundancy and contamination in hairpin-bisulfite PCR, Nucl Acids Res 32(17):e135, 4 pages.
Minton, 2011, Mutation Surveyor: software for DNA sequence analysis, Meth Mol Biol 688:143-53.
Miyake, 2009, PIK3CA gene mutations and umplification in uterine cancers, Canc Lett 261:120-126.
Miyazaki, 2009, Characterization of deletion breakpoints in patients with dystrophinopathy carrying a deletion of exons 45-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, Deliminate—a fast and efficient methods for loss-less compression of genomice sequences, Bioinformatics 28(19):2527-2529.
Moudrianakis, 1965, Base Sequence Determination in Nucleic Acids with the Electron Microscope, III. Chemistry and Microscopy of Guanine-Labeled DNA, PNAS, 53:564-71.
Mullan, 2002, Multiple sequence alignment—the gateway to further analysis, Brief Bioinform 3(3):303-5.
Munne, 2012, Preimplantation genetic diagnosis for aneuploidy and translocations using array comparative genomic hybridization, Curr Genomics 13(6):463-470.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Nelson, 1989, Bifunctional oligonucleotide probes synthesized using a novel CPG support are able to detect single base pair mutations, Nucl Acids Res 17(18):7187-7194.
Ng, 2009, Targeted capture and massively parallel sequencing of 12 human exomes, Nature 461(7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nielsen, 1999, Peptide Nucleic Acids, Protocols and Applications (Norfolk: Horizon Scientific Press, 1-19).
Nilsson, 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.
Nuttle, 2013, Rapid and accurate large-scale genotyping of duplicated genes and discovery of interlocus gene conversions, Nat Meth 10(9):903-909.
Nuttle, 2014, Resolving genomic disorder-associated breakpoints within segmental DNA duplications using massively parallel sequencing, Nat Prot 9(6):1496-1513.
O'Roak, 2012, Multiplex targeted sequencing identifies recurrently mutated genes in autism spectrum disorders, Science 338(6114):1619-1622.
Oefner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.

Okoniewski, 2013, Precise breakpoint localization of large genomic deletions using PacBio and Illumina next-generation sequencers, Biotechniques 54(2):98-100.
Okou, 2007, Microarray-based genomic selection for high-throughput reseuqencing, Nat Meth 4(11):907-909.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res 3:2985-2999.
Ostrer, 2001, A genetic profile of contemporary Jewish populations, Nat Rev Genet 2(11):891-8.
Owens, 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130, 27 pages.
Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bioinformatics 16(6):548-57.
Pearson, 1988, Improved tools for biological sequence comparison, PNAS 85(8):2444-8.
Pertea, 2003, TIGR gene indices clustering tools (TGICL), Bioinformatics 19(5):651-52.
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2007, Multiplex amplificaiton of large sets of human exons, Nat Meth 4(11):931-936.
Porreca, 2013, Analytical performance of a Next-Generation DNA sequencing-based clinical workflow for genetic carrier screening, American Society of Human Genetics 63rd Annual Meeting, Abstract, Oct. 22, 2013, 2 pages.
Pourmand, 2006, PathgoenMIPer: a tool for the design of molecular inversion probes, BMC informatics 7:500, 10 pages.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Qiagen, 2011, Gentra Puregene handbook, 3d Ed., 72 pages.
Quail, 2010, DNA: Mechanical Breakage, In Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.
Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLoS ONE 3:e3373, 12 pages.
Roberts, 1980, Restriction and modification enzymes and their recognition sequences, Nucleic Acids Res 8(1):r63-r80.
Rodriguez, 2010, Constructions from Dots and Lines, Bull Am Soc Inf Sci Tech 36(6):35-41.
Rosendahl, 2013, CFTR, SPINK1, CTRC and PRSS1 variants in chronic pancreatitis: is the role of mutated CFTR overestimated?, Gut 62:582-592.
Rothberg, 2011, An integrated semiconductor device enabling non-optical genome sequencing, Nature 475:348-352.
Rowntree, 2003, The phenotypic consequences of CFTR mutations, Ann Hum Gen 67:471-485.
Saihan, 2009, Update on Usher syndrome, Curr Op Neurology 22(1):19-24.

(56) References Cited

OTHER PUBLICATIONS

Sanger, 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Sargent, 1987, Isolation of differentially expressed genes, Meth Enzym 152:423-432.
Sauro, 2004, How Do You Calculate a Z-Score/ Sigma Level?, https://www.measuringusability.com/zcalc.htm (online publication), 3 pages.
Sauro, 2004, What's a Z-score and Why Use It in Usability Testing?, https://www.measuringusability.com/z.htm (online publication), 4 pages.
Schadt, 2010, A window into third-generation sequencing, Human Mol Genet 19(R2):R227-40.
Schatz, 2010, Assembly of large genomes using second-generation sequencing, Genome Res., 20:1165-1173.
Schiffman, 2007, Adapting molecular inversion probe (MIP) technology for allele quantification in childhood leukemia, Journal of Clinical Oncology, 25, p. 530, 5 pages.
Schiffman, 2009, Molecular inversion probes reveal patterns of 9p21 deletion and copy number aberrations in childhood leukemia, Cancer Genetics and Cytogenetics 193:9-18.
Schneeberger, 2011, Reference-guided assembly of four diverse Arabidopsis thaliana genomes, PNAS 108(25):10249-10254.
Schouten, 2002, Relative Quantification of 40 Nucleic Acid Sequences by Multiplex Ligation-Dependent Probe Amplification, Nucle Acids Res 30 (12):257, 13 pages.
Schrijver, 2005, Diagnostic testing by CFTR gene mutation analysis in a large group of Hispanics, J Mol Diag 7(2):289-299.
Schuette, 1995, Sequence analysis of phosphorothioate oligonucleotides via matrix-assisted laser desorption ionization time-of-flight mass spectrometry, J Pharm Biomed Anal 13:1195-1203.
Schwartz, 2009, Identification of cystic fibrosis variants by polymerase chain reaction/oligonucleotide ligation assay, J Mol Diag 11(3):211-15.
Schwartz, 2011, Clinical utility of single nucleotide polymorphism arrays, Clin Lab Med 31(4):581-94.
Sequeira, 1997, Implementing generic, object-oriented models in biology, Ecological Modeling 94.1:17-31.
Shagin, 2002, A novel method for SNP detection, Genome Res 12:1935-1942.
Shen, 2011, High quality DNA sequence capture of 524 disease candidate genes, PNAS 108(16):6549-6554.
Shen, 2013, Multiplex capture with double-stranded DNA probes, Genome Medicine 5(50):1-8.
Sievers, 2011, Fast, scalable generation of high-quality protein multiple sequence alignments using Clustal Omega, Mol Syst Biol 7:539, 6 pages.
Simpson, 2009, ABySS: A parallel assembler for short read sequence data, Genome Res., 19(6):1117-23.
Slater, 2005, Automated generation of heuristics for biological sequence comparison, BMC Bioinformatics 6:31, 11 pages.
Smirnov, 1996, Sequencing oligonucleotides by exonuclease digestion and delayed extraction matrix-assisted laser desorption ionization time-of-flight mass spectrometry, Anal Biochem 238:19-25.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 2010, Highly-multiplexed barcode sequencing: an efficient method for parallel analysis of pooled samples, Nucleic Acids Research 38(13):e142, 8 pages.
Soni, 2007, Progress toward ultrafast DNA sequencing using solid-state nanopores, Clin Chem 53(11):1996-2001.
Cock, 2010, The Sanger FASTQ file format for sequences with quality scores, and the Solexa/Illumina FASTQ variants, Nucleic Acids Res 38(6):1767-1771.
Collins, 2004, Finishing the euchromatic sequence of the human genome, Nature 431(7011):931-45.
Craig, 1997, Removal of repetitive sequences from FISH probes, Hum Genet 100:472.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355-362.
Cronin, 1996, Cystic Fibrosis Mutation Detection by Hybridization to Light-Generated DNA Probe Arrays Human Mutation 7:244-255.
Dahl, 2005, Multiplex amplification enabled by selective circularization of large sets of genomic DNA fragments, Nucleic Acids Res 33(8):e71, 7 pages.
Daly, 2007, Multiplex Assay for Comprehensive Genotyping of Genes Involved in Drug Metabolism, Excretion, and Transport, Clinical Chemistry, 53:7:1222-1230.
Danecek, 2011, The variant call format and VCFtools, Bioinformatics 27(15):2156-2158.
De la Bastide, 2007, Assembling genome DNA sequences with PHRAP, Current Protocols in Bioinformatics 17:11.4.1-11.4.15, 15 pages.
Delcher, 1999, Alignment of whole genomes, Nuc Acids Res 27(11):2369-2376.
Den Dunnen, 2003, Mutation Nomenclature, Curr Prot Hum Genet 7.13.1-7.13.8, 8 pages.
Deng, 2009, targeted bisulfite sequencing reveals changes in DNA methylation, Nat Biotech 27(4):353-360.
Deng, 2012, Supplementary Material, Nature Biotechnology, S1-1-S1-1 1, Retrieved from the Internet on Oct. 24, 2012, 12 pages.
Deorowicz, 2013, Data compression for sequencing data, Alg for Mole Bio 8:25, 13 pages.
Diep, 2012, Library-free methylation sequencing with bisulfite padlock probes, Nature Methods 9:270-272 (and supplemental information).
DiGuistini, 2009, De novo sequence assembly of a filamentous fungus using Sanger, 454 and Illumina sequence data, Genome Biology, 10:R94, 12 pages.
Dolinsek, 2013, Depletion of unwanted nucleic acid templates by selection cleavage: LNAzymes, catalytically active oligonucleotides containing locked nucleic acids, open a new window for detecting rare microbial community members, App Env Microbiol 79(5):1534-1544.
Dong, 2011, Mutation surveyor: An in silico tool for sequencing analysis, Methods Mol Biol 760:223-37.
Dou, 2012, Reference-free SNP calling: improved accuracy by preventing incorrect calls from repetitive genomic regions, Biology Direct 7:17.
Drmanac, 1992, Sequencing by hybridization: towards an automated sequencing of one million M13 clones arrayed on membranes, Elctrophoresis 13:566-573.
Dudley, 2009, A quick guide for developing effective bioinformatics programming skills, PLoS Comp Biol 5(12):e1000589, 7 pages.
Ericsson, 2008, A dual-tag microarray platform for high-performance nucleic acid and protein analyses, Nucl Acids Res 36:e45, 9 pages.
Fares, 2008, Carrier frequency of autosomal-recessive disorders in the Ashkenazi Jewish population: should the rationale for mutation choice for screening be reevaluated?, Prenatal Diagnosis 28:236-41.
Faulstich, 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014, 2 pages.
Fitch, 1970, Distinguishing homologs from analogous proteins, Syst Biol 19(2):99-113.
Flaschker, 2007, Description of the mutations in 15 subjects with variant forms of maple syrup urine disease, J Inherit Metab Dis 30:903-909.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60, 28 pages.
Fu, 2010, Repeat subtraction-mediated sequence capture from a complex genome, The Plant Journal, 62:898-909.

(56) References Cited

OTHER PUBLICATIONS

Furtado, 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Gemayel, 2010, Variable tandem repeats accelerate evolution of coding and regulatory sequences, Ann Rev Genet 44:445-77.
Giusti, 1993, Synthesis and Characterization of f'-Fluorescent-dye-labeled Oligonucleotides, PCR Meth Appl 2:223-227.
Glover, 1995, Sequencing of oligonucleotides using high performance liquid chromatography and electrospray mass spectrometry, Rapid Com Mass Spec 9:897-901.
Gnirke, 2009, Solution hybrid selection with ultra-long oligonucleotides for massively parallel targeted sequencing, nature biotechnology 27:182-9.
Goto, 1994, A Study on Development of a Deductive Object-Oriented Database and Its Application to Genome Analysis, PhD Thesis, Kyushu University, Kyushu, Japan, 106 pages.
Goto, 2010, BioRuby: bioinformatics software for the Ruby programming language, Bioinformatics 26(20):2617-2619.
Green, 2005, Suicide polymerase endonuclease restriction, a novel technique for enhancing PCR amplification of minor DNA template, Appl Env Microbiol 71(8):4721-4727.
Guerrero-Fernandez, 2013, FQbin: a compatible and optimize dformat for storing and managing sequence data, IWBBIO Proceedings, Granada 337-344.
Gupta, 1991, A general method for the synthesis of 3'-sulfhydryl and phosphate group containing oligonucleotides, Nucl Acids Res 19(11):3019-3025.
Gupta, 2014, Expanding the genetic toolkit: ZFNs, TALENs, and CRISPR-Cas9, J Clin Invest 124(10):4154-4161.
Gustincich, 1991, A fast method for high-quality genomic DNA extraction from whole human blood, BioTechniques 11(3):298-302.
Gut, 1995, A procedure for selective DNA alkylation and detection by mass spectrometry, Nucl Acids Res 23(8):1367-1373.
Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Hardenbol, 2005, Highly multiplexed molecular inversion probe genotyping: over 10,000 targeted SNPs genotyped in a single tube assay, Genome Res 15:269-75.
Harris, 2006, Defects can increase the melting temperature of DNA-nanoparticle assemblies, J Phys Chem B 110(33):16393-6.
Harris, 2008, Helicos True Single Molecule Sequencing (tSMS) Science 320:106-109.
Zhao, 2009, PGA4genomics for comparative genome assembly based on genetic algorithm optimization, Genomics 94(4):284-6.
Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30(8):1073-1080.
Zhulidov, 2004, Simple cDNA normalization using kamchatka crab duplex-specific nuclease, Nucl Acids Res 32(3):e37, 8 pages.
Zimmerman, 2010, A novel custom resequencing array for dilated cardiomyopathy, Gen Med 12(5):268-78.
Zimran, 1990, A glucocerebrosidase fusion gene in Gaucher disease, J Clin Invest 85:219-222.
Zuckerman, 1987, Efficient methods for attachment of thiol specific probes to the 3'-ends of synthetic oligodeoxyribonucleotides, Nucl Acid Res 15(13):5305-5321.
Sonnhammer, 2002, Orthology, paralogy and proposed classification for paralog subtypes, Trends in Genetics, 18(12):619-620.

Spanu, 2010, Genome expansion and gene loss in powdery mildew fungi reveal tradeoffs in extreme parasitism, Science 330(6010):1543-46.
Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.
Streit, 2003, CFTR gene: molecular analysis in patients from South Brazil, Molecular Genetics and Metabolism 78:259-264.
Strom, 2005, Mutation detection, interpretation, and applications in the clinical laboratory setting, Mutat Res 573:160-67.
Summerer, 2009, Enabling technologies of genomic-scale sequence enrichment for targeted high-throughput sequencing, Genomics 94(6):363-8.
Summerer, 2010, Targeted High Throughput Sequencing of a Cancer-Related Exome Subset by Specific Sequence Capture With a Fully Automated Microarray Platform, Genomics 95(4):241-246.
Sunnucks, 1996, Microsatellite and chromosome evolution of parthenogenetic sitobion aphids in Australia, Genetics 144:747-756.
Tan, 2014, Clinical outcome of preimplantation genetic diagnosis and screening using next generation sequencing, GigaScience 3(30):1-9.
Tarhini, 2018, Predictive and on-treatment monitoring biomarkers in advanced melanoma: Moving toward personalized medicine, Cancer Treatment Reviews, 71:8-18.
Thauvin-Robinet, 2009, The very low penetrance of cystic fibrosis for the R117H mutation: a reappraisal for genetic counseling and newborn screening, J Med Genet 46:752-758.
Thiyagarajan, 2006, PathogenMIPer: a tool for the design of molecular inversion probes to detect multiple pathogens, BMC Bioinformatics 7:500, 10 pages.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217, 10 pages.
Thorstenson, 1998, An Automated Hydrodynamic Process for Controlled, Unbiased DNA Shearing, Genome Res 8(8):848-855.
Thorvaldsdottir, 2012, Integrative Genomics Viewer (IGV): high-performance genomics data visualization and exploration, Brief Bioinform 24(2):178-92.
Tkachuk, 1990, Detection of bcr-abl Fusion in Chronic Myelogeneous Leukemia by in Situ Hybridization, Science 250:559-562.
Tobler, 2005, The SNPlex Genotyping System: A Flexible and Scalable Platform for SNP Genotyping, J Biomol Tech 16(4):398-406.
Tokino, 1996, Characterization of the human p57 KIP2 gene: alternative splicing, insertion/deletion polymorphisms in VNTR sequences in the coding region, and mutational analysis, Human Genetics 96:625-31.
Treangen, 2011, Repetitive DNA and next-generation sequencing: computational challenges and solutions, Nat Rev Gen 13(1):36-46.
Turner, 2009, Massively parallel exon capture and library-free resequencing across 16 genomes, Nat Meth 6:315-316.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013, 2 pages.
Umbarger, 2014, Next-generation carrier screening, Gen Med 16(2):132-140.
Veeneman, 2012, Oculus: faster sequence alignment by streaming read compression, BMC Bioinformatics 13:297, 8 pages.
Wahl, 1979, Efficient transfer of large DNA fragments from agarose gels to diazobenzyloxymethyl-paper and rapid hybridization by using dextran sulfate, PNAS 76:3683-3687.
Wallace, 1979, Hybridization of synthetic oligodeoxyribonucteotides to dp x 174DNA:the effect of single base pair mismatch, Nucl Acids Res 6:3543-3557.
Wallace, 1987, Oligonucleotide probes for the screening of recombinant DNA libraries, Meth Enz 152:432-442.
Wang, 2005, Allele quantification using molecular inversion probes (MIP), Nucleic Acids Res 33(21):e183, 14 pages.

(56) References Cited

OTHER PUBLICATIONS

Wang, 2007, Analysis of molecular inversion probe performance for allele copy number determination, Genome Biology, 8(11):R246.1-R246.14.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Waszak, 2010, Systematic inference of copy-number genotypes from personal genome sequencing data reveals extensive olfactory gene content diversity, PLoS Comp Biol 6(11):e1000988, 20 pages.
Watson, 2004, Cystic fibrosis population carrier screening: 2004 revision of American College of Medical Genetics mutation panel, Genetics in Medicine 6(5):387-391.
Williams, 2003, Restriction endonucleases classification, properties, and applications, Mol Biotechnol 23(3):225-43.
Wirth, 1999, Quantitative analysis of survival motor neuron copies, Am J Hum Genet 64:1340-1356.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973-7979.
Wu, 1998, Sequencing regular and labeled oligonucleotides using enzymatic digestion and ionspray mass spectrometry, Anal Biochem 263:129-138.
Wu, 2001, Improved oligonucleotide sequencing by alkaline phosphatase and exonuclease digestions with mass spectrometry, Anal Biochem 290:347-352.
Xu, 2012, FastUniq: A fast de novo duplicates removal tool for paired short reads, PLoS One 7(12):e52249, 6 pages.
Yau, 1996, Accurate diagnosis of carriers of deletions and duplications in Duchenne/Becker muscular dystrophy by fluorescent dosage analysis, J Med Gen 33(7):550-8.
Ye, 2009, Pindel: a pattern growth approach to detect break points of large deletions and medium size insertions from paired-end short reads, Bioinformatics 25(21):2865-2871.
Yershov, 1996, DNA analysis and diagnostics on oligonucleotide microchips, PNAS 93:4913-4918.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28, 9 pages.
Yoshida, 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18(5):821-829.
Zhang, 2011, Is Mitochondrial IRNAphe Variant m.593T.Ca Synergistically Pathogenic Mutation in Chinese LHON Families with m.11778G.A? PLoS ONE 6(10):e26511, 8 pages.
Harris, 2008, Single-molecule DNA sequencing of a viral genome, Science 320(5872):106-9.
Heger, 2006, Protonation of Cresol Red in Acidic Aqueous Solutions Caused by Freezing, J Phys Chem B 110(3):1277-1287.
Heid, 1996, Real time quantitative PCR, Genome Res 6:986-994.
Hiatt, 2013, Single molecule molecular inversion probes for targeted, high-accuracy detection of low-frequency variation, Genome Res 23:843-54.
Hodges, 2007, Genome-wide in situ exon capture for selective resequencing, Nat Genet 39(12):1522-7.
Holland, 2008, BioJava: an open-source framework for bioinformatics, Bioinformatics 24(18):2096-2097.
Homer, 2008, Resolving Individuals Contributing Trace Amounts of DNA to Highly Complex Mixtures Using High-Density SNP Genotyping Microarrays. PLoS One 4(8):e1000167, 9 pages.
Homer, 2009, BFAST: An alignment tool for large scale genome resequencing, PLoS ONE 4(11):e7767, 12 pages.
Housley, 2009, SNP discovery and haplotype analysis in the segmentally duplicated DRD5 coding region, Ann Hum Genet 73(3):274-282.
Huang, 2008, Comparative analysis of common CFTR polymorphisms poly-T, TGrepeats and M470V in a healthy Chinese population, World J Gastroenterol 14(12):1925-30.
Husemann, 2009, Phylogenetic Comparative Assembly, Algorithms in Bioinformatics: 9th International Workshop, Salzberg & Warnow, Eds. Springer-Verlag, Berlin, Heidelberg, pp. 145-156.
Illumina, 2010, De Novo assembly using Illumina reads, Technical Note, 8 pages.
International Human Genome Sequencing Consortium, 2004, Finishing the euchromatic sequence of the human genome, Nature 431:931-945.
Iqbal, 2012, De novo assembly and genotyping of variants using colored de Bruijn graphs, Nature Genetics 44:226-232.
Isosomppi, 2009, Disease-causing mutations in the CLRN1 gene alter normal CLRN1 protien trafficking to the plasma membrane, Mol Vis 15:1806-1818.
Jaijo, 2010, Microarray-based mutation analysis of 183 Spanish families with Usher syndrome, Invest Ophthalmol Vis Sci 51(3):1311-7.
Jensen, 2001, Orthologs and paralogs—we need to get it right, Genome Biol 2(8):1002-1002.3.
Jones, 2008, Core signaling pathways in human pancreatic cancers revealed by global genomic analyses, Science 321(5897):1801-1806.
Kambara, 1988, Optimization of Parameters in a DNA Sequenator Using Fluorescence Detection, Nature Biotechnology 6:816-821.
Kennedy, 2013, Accessing more human genetic variation with short sequencing reads, American Society of Human Genetics 63rd Annual Meeting, Abstract, Oct. 22, 2013, 2 pages.
Kent, 2002, BLAT—The BLAST-like alignment tool, Genome Res 12(4): 656-664.
Kerem, 1989, Identification of the cystic fibrosis gene: genetic analysis, Science 245:1073-1080.
Kinde, 2012, FAST-SeqS: a simple an effective method for detection of aneuploidy by massively parallel sequencing, PLoS One 7(7):e41162, 8 pages.
Kircher, 2010, High-througput DNA sequencing—concepts and limitations, Bioassays 32:524-36.
Kirpekar, 1994, Matrix assisted laser desorption/ionization mass spectrometry of enzymatically synthesized RNA up to 150 kDa, Nucl Acids Res 22:3866-3870.
Klein, 2011, LOCAS—A low coverage sequence assembly tool for re-sequencing projects, PLoS One 6(8):e23455, 10 pages.
Kneen, 1998, Green fluorescent protein as a noninvasive intracellular pH indicator, Biophys J 74(3):1591-99.
Koboldt, 2009, VarScan: variant detection in massively parallel sequencing of individual and pooled samples, Bioinformatics 25:2283-85.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125(2):219-229.
Krishnakumar, 2008, A comprehensive assay for targeted multiplex amplification of human DNA sequences, PNAS 105:9296-301.
Kumar, 2010, Comparing de novo assemblers for 454 transcriptome data, Genomics 11:571 (12 pages).
Kurtz, 2004, Versatile and open software for comparing large genomes, Genome Biol 5:R12, 9 pages.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25, 10 pages.
Larkin, 2007, Clustal W and Clustal X version 2.0, Bioinformatics, 23(21):2947-2948.
Lecompte, 2001, Multiple alignment of complete sequences (MACS) in the post-genomic era, Gene 270(1-2):17-30.

(56) References Cited

OTHER PUBLICATIONS

Li, 2003, DNA binding and cleavage by the periplasmic nuclease Vvn: a novel structure with a known active site, EMBO J 22(15):4014-4025.
Li, 2008, SOAP: short oligonucleotide alignment program, Bioinformatics 24(5):713-14.
Li, 2009, Fast and accurate short read alignment with Burrows-Wheeler transform, Bioinformatics, 25 (14):1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, Fast and accurate long-read alignment with Burrows-Wheeler transform, Bioinformatics 26(5):589-95.
Li, 2011, Improving SNP discovery by base alignment quality, Bioinformatics 27:1157, 2 pages.
Li, 2011, Single nucleotide polymorphism genotyping and point mutation detection by ligation on microarrays, J Nanosci Nanotechnol 11(2):994-1003.
Li, 2012, A new approach to detecting low-level mutations in next-generation sequence data, Genome Biol 13:1-15.
Li, 2014, HUGO: Hierarchical mUlti-reference Genome cOmpression for aligned reads, JAMIA 21:363-373.
Lin, 2008, ZOOM! Zillions Of Oligos Mapped, Bioinformatics 24:2431-2437.
Lin, 2010, A molecular inversion prove assay for detecting alternative splicing, BMC Genomics 11(712):1-14.
Lin, 2012, Development and evaluation of a reverse dot blot assay for the simultaneous detection of common alpha and beta thalassemia in Chinese, Blood Cells Molecules, and Diseases 48(2):86-90.

\* cited by examiner

METHODS FOR DETERMINING CARRIER STATUS

CROSS-REFERENCE TO RELATED APPLICATIONS

This application is a Continuation Application of U.S. patent application Ser. No. 14/057,673, filed on Oct. 18, 2013, the contents of which are incorporated herein by reference in their entirety.

FIELD

The present invention relates generally to genetic testing, and, more particularly, to methods for determining carrier or disease status with respect to a particular disease or condition.

BACKGROUND

Genetic counseling is the process by which individuals, typically prospective parents, are advised regarding the likelihood of transmitting an inherited or genetic disorder to any future offspring. To assist in the process, individuals seeking counseling typically undergo a number of tests that assess indications of genetic disorders. These tests may include, for example, screening assays that detect clinically significant variations in various biomarkers. For example, carrier screening can determine if members of a couple are both carriers of a recessive genetic disorder. With this information, the couple can learn or rule out that they are at risk for having children with the genetic disorder.

Some currently available tests screen for autosomal recessive disorders, including spinal muscular atrophy (SMA). Spinal muscular atrophy (SMA) is an autosomal recessive disease characterized by degeneration of motor neurons in the anterior horn of a spinal cord, leading to muscular paralysis and atrophy. The prognosis for SMA may vary on an individual basis. However, the majority of patients children diagnosed with SMA do not reach the age of 10. SMA is the second most common autosomal recessive inherited disorder in humans and the most common genetic cause of infant mortality.

SMA is caused by the homozygous deletion or mutations of the survival motor neuron gene (SMN), including telomeric SMN (SMN1) and centromeric SMN (SMN2) genes. SMA has a carrier frequency of approximately 1 in 40, which is attributable primarily to SMN1 copy number loss produced by either deletion of part or all of SMN1, or conversion of SMN1 to the SMN2 gene, a linked paralog that encodes an identical protein but is poorly expressed due to a silent coding variant that disrupts proper splicing.

Current methods for clinical SMA carrier screening include multiplex ligation-dependent probe amplification (MLPA) for assessing the copy number state of SMN1 in a manner that distinguishes between SMN1 and SMN2, typically by interrogating the exon 7 variant that differs between the paralogs. MLPA is a variation of multiplex polymerase chain reaction (PCR) and permits multiple targets to be amplified with only a single primer pair.

Although current MLPA-based carrier screening assays may be relatively sensitive and specific, they have significant drawbacks. For example, one problem with current MLPA-based assays is that they generally quantify only the nucleotide difference in exon 7 of the SMN1/SMN2 genes. However, it has been found that SMA in approximately 6% of affected patients is caused by point mutations at other exons in which SMN1 is present. As such, MLPA-based assays may miss detection of such point mutations, possibly resulting in inaccurate screening results. Another problem is that MLPA-based assays are time consuming and relatively low-throughput.

SUMMARY

The invention solves problems associated with current carrier screening assays by providing molecular inversion probes for capturing at least one genomic region known or suspected to be associated with a disease and subsequently sequencing the captured DNA to determine the copy number state of the captured DNA. In certain aspects, the captured DNA may be sequenced by known high-throughput sequence methods or techniques. The carrier status for the disease can then be determined based on the identified copy number state. In particular, the copy number state may be indicative of whether the patient is a carrier of a particular disease or condition for which copy number variation is diagnostic, such as an autosomal recessive trait (e.g., spinal muscular atrophy). For example, it can be determined whether copy number variation exists in the genomic regions of interest based on the identified copy number, thereby providing a method for determining whether the patient is a carrier of such an autosomal recessive trait.

Accordingly, the invention overcomes the problems of current carrier screening assays, particularly MLPA-based assays, based, at least in part, on compatibility with automated high-throughput screening. In particular, the invention provides the sensitivity and specificity for detection of copy number variation in SMN1 and/or SMN2, similar to MLPA-based methods, by utilizing molecular inversion probes. Additionally, by using high-throughput screening methods, the invention allows detection of deleterious SMN1 point mutations and indels that would otherwise be missed by MLPA and related approaches, thereby providing more reliable and accurate diagnosis.

In certain aspects, the invention provides a method for determining copy number state of one or more genes in a sample. The method includes exposing a sample to a plurality of molecular inversion probes capable of capturing DNA from at least one genomic region suspected of having an altered copy number, and at least one internal control DNA known or suspected to have a stable copy number. The at least one genomic region may be associated with a particular locus, such as, for example, SMN1 or SMN2, that is associated with a condition or disease.

In embodiments that utilize molecular inversion probes, any molecular inversion probe may be used. An exemplary MIP is a single-stranded probe about 70 nucleotides in length, composed of a universal core of 30 nucleotides that is flanked by specific 20-nucleotide targeting sequences on each side, i.e. targeting arms. However, the length and composition of the probe can vary to most adequately capture the desired target sequence. The targeting arms are designed to hybridize to specific genomic regions upstream and downstream of a target sequence of interest located on the nucleic acid fragment. After the target sequence of interest is isolated between the target arms, the target sequence can be analyzed. Although each MIP captures one target of interest for analysis, multiple probes can be combined into a single vessel containing sample for a multiplexed assay that simultaneously examines multiple target loci.

Upon capturing DNA that binds the molecular inversion probes, the captured DNA is sequenced and further analyzed to determine copy number state for use in determining carrier status of a disease in which copy number variation is diagnostic. The sequencing results in a plurality of reads for both the genomic region suspected of having an altered copy number and the internal control DNA.

Read counts obtained in the sequencing step are normalized for the genomic region with respect to the internal control DNA. The normalized read counts for the genomic region and the control DNA are compared with one another to obtain a ratio of normalized read count of genomic regions of interest/normalized read count of internal control DNA. The copy number state of the genomic region can then be determined based upon the ratio (i.e. difference between the normalized read counts).

The copy number state can be used to determine the carrier status of an individual from which the sample was obtained. In particular, the copy number state may be indicative of whether the patient is a carrier of a particular disease or condition for which copy number variation is diagnostic. Copy-number variations (CNVs), a form of structural variation, are alterations of the DNA of a genome that results in the cell having an abnormal number of copies of one or more sections of the DNA. CNVs correspond to relatively large regions of the genome that have been deleted (fewer than the normal number) or duplicated (more than the normal number) on certain chromosomes. Some diseases are associated with CNVs of particular genes or gene fragments. For example, copy number variation in the SMN1 and/or SMN2 gene is closely associated with spinal muscular atrophy (SMA), an autosomal recessive trait. Accordingly, variation in the copy number state may indicate the presence of an autosomal recessive trait, thereby determining that the patient is a carrier of such an autosomal recessive trait.

In certain aspect, it can be determined whether copy number variation exists in the genomic regions of interest based on the calculated ratio of normalized read count of genomic regions of interest/normalized read count of internal control DNA. For example, copy number variation generally exists if there is a statistical difference between the normalized read counts for the genomic region the control DNA (i.e. a ratio outside of a range of 0.8 to 1.2). Similarly, copy number variation does not exist if there is little or no statistical difference between the normalized read counts for the genomic region the control DNA (i.e. a ratio within the range of 0.8 to 1.2).

The invention may be used to determine carrier status for other autosomal recessive traits, including, but not limited to, cystic fibrosis, sickle cell anemia, tay sachs disease, Familial hyperinsulinism, Canavan Disease, Maple Syrup Urine Disease, Bloom's Syndrome, Usher Syndrome type IIIA, Dihydrolipoamide dehydrogenase deficiency, Fanconi anemia group C, Familial dysautonomia, Mucolipidosis Type IV, Usher Syndrome Type IV, Nieman-Pick disease type A/B, Walker Warburg syndrome, and Joubert Syndrome.

In a related aspect, the invention provides a method of determining copy number between two paralogous genes. The method includes exposing a sample including a first genetic locus, a second genetic locus, and at least one control genetic locus to a plurality of molecular inversion probes. At least some of the probes are capable of hybridizing with one or more of the first genetic locus, the second genetic locus, and the control genetic locus. The first and second genetic locus may be associated with a particular disease for which copy number variation is diagnostic. Upon obtaining DNA that is hybridized to a member of the plurality of molecular inversion probes, the obtained DNA is sequenced (e.g., next-generation sequencing method) and read counts for each of the first genetic locus and the second genetic locus are normalized with respect to the at least one control genetic locus. The normalized read counts for each of the first genetic locus and the second genetic locus are then compared to normalized read counts for one or more control samples with a known number of copies of the first genetic locus and the second genetic locus. Based on the comparison, relative copy numbers of the first genetic locus and the second genetic locus can be determined. The determined copy numbers can then be used to determine the carrier status of an individual from which the sample was obtained (i.e. whether the patient is a carrier of the disease).

In another related aspect, the invention provides a method for the determination of carrier status with respect to one or more conditions. The method includes exposing a sample to a plurality of molecular inversion probes, at least some of which are capable of hybridizing to DNA of a first locus or DNA of a second locus. DNA in the sample that is hybridized to a member of the plurality of probes is obtained and then sequenced (e.g. next-generation sequencing methods) to obtain sequence read counts for the first locus and the second locus. The read counts are normalized with respect to a control locus, the copy number of which is stable or known. The copy number status of the first locus and the second locus is then inferred based, at least in part, on a comparison of the normalized read counts for the first locus and the second locus with a standard.

DETAILED DESCRIPTION

Figure 1:
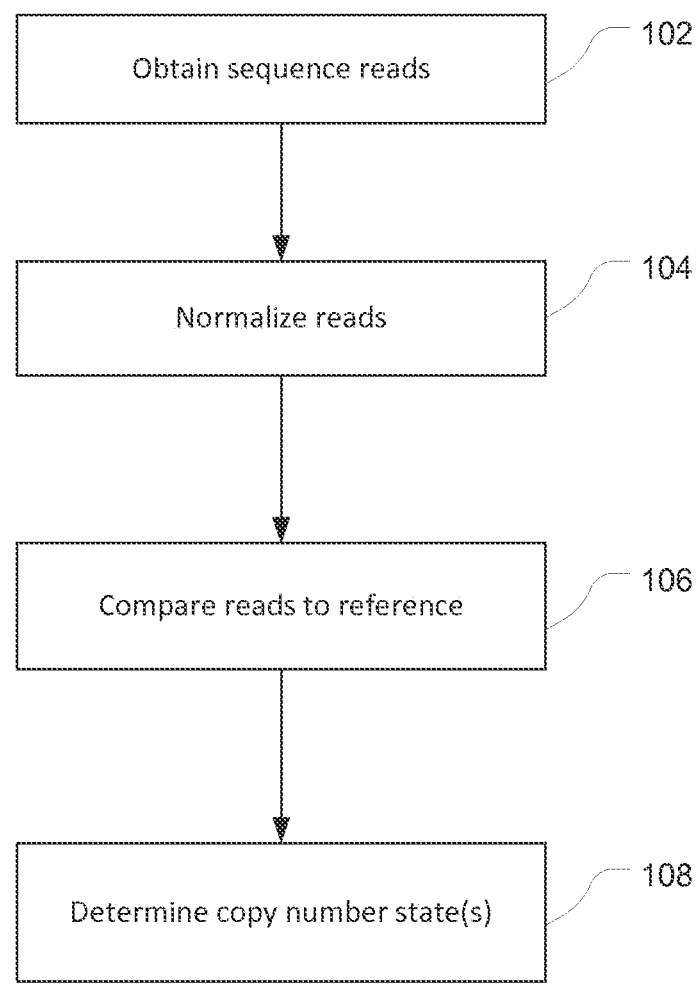
FIG. 1 is a diagram of methods of the invention.

The invention generally relates to methods for determining carrier status with respect to a condition or disease, particularly an autosomal recessive trait. In certain embodiments, methods of the invention include determining copy number state of one or more genes in a sample. The methods includes exposing a sample to a plurality of molecular inversion probes capable of capturing DNA from at least one genomic region suspected of having an altered copy number, and at least one internal control DNA known or suspected to have a stable copy number. In some embodiments, the at least one genomic region may be associated with a particular locus, such as, for example, SMN1 or SMN2, that is associated with a condition or disease. The methods further include capturing and sequencing DNA that binds to the molecular inversion probes, normalizing read counts obtained in the sequencing step for the least one genomic region with respect to the internal control DNA, and determining a copy number state of the at least one genomic region based on a comparison between the normalized read counts of the genomic region and read counts for a control diploid locus.

By way of overview, methods of the invention involve obtaining one or more samples including nucleic acids. The nucleic acids, including genomic nucleic acids, of each sample are fragmented and/or denatured so as to render the nucleic acid single stranded for hybridization to a capture probe, such as a molecular inversion probe. As described in greater detail herein, each sample is exposed to a plurality of molecular inversion probes to hybridize or bind with at least one genomic region of interest (e.g. locus) located on the nucleic acid fragments. After capture of the genomic region of interest, the captured region is subjected to an enzymatic gap-filling and ligation step, and further subjected to amplification based on sample-specific barcode polymerase chain reaction (PCR). The resulting barcodes PCRs for each sample are then combined into a master pool and quantified. Analysis of the captured regions of interest involves sequencing, e.g., with a next-generation sequencer, and determining copy number states of the genomic regions of interest based on the sequencing readout.

Nucleic acids suitable for use in aspects of the invention include but are not limited to genomic DNA, genomic RNA, synthesized nucleic acids, whole or partial genome amplification product, and high molecular weight nucleic acids, e.g. individual chromosomes. Genomic DNA and genomic RNA constitute the total genetic information of an organism. Genomic nucleic acids molecules are generally large, and in most organisms are organized into DNA-protein complexes called chromosomes, which the exception of viruses that have RNA genomes. Genomic RNA also includes, for example, RNA transcribed from DNA, unprocessed transcripts, mRNAs, and cDNAs. Sometimes the quality and quantity of genomic nucleic acids obtained from samples precludes their usefulness in large scale genotyping studies. To overcome this problem, use of whole genome amplification products and partial genome amplification products allows for characterization of the genome of a sample even if the quantity and quality of the genomic nucleic acid is limited.

Samples and Obtaining Nucleic Acid

In certain aspects, methods of the invention may involve obtaining a sample. The sample is typically a tissue or body fluid that is obtained in any clinically acceptable manner. A tissue is a mass of connected cells and/or extracellular matrix material, e.g. skin tissue, endometrial tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed. Samples are also obtained from the environment (e.g., air, agricultural, water and soil); and research samples (e.g., products of a nucleic acid amplification reaction, or purified genomic DNA, RNA, proteins, etc.).

Isolation, extraction or derivation of genomic nucleic acids is performed by methods known in the art. Isolating nucleic acid from a biological sample generally includes treating a biological sample in such a manner that genomic nucleic acids present in the sample are extracted and made available for analysis. Any isolation method that results in extracted/isolated genomic nucleic may be used in the practice of the present invention.

Nucleic acids may be obtained by methods known in the art. Generally, nucleic acids are extracted using techniques, such as those described in Sambrook. J., Fritsch, E. F., and Maniatis, T. (1989) Molecular Cloning: A Laboratory Manual. 2nd ed. Cold Spring Harbor, NY:Cold Spring Harbor Laboratory.), the contents of which are incorporated by reference herein. Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). Several protocols have been developed to extract genomic DNA from blood.

There are also numerous kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), Qiagen Inc. (Valencia, Calif.). Autogen (Holliston, MA); Beckman Coulter (Brea, CA), (AutoGenFlex STAR robot with Qiagen FlexiGene chemistry. For example, Autogen manufactures FlexStar automated extraction kits used in combination with Qiagen FlexiGene Chemistry, and Beckeman Coulter manufactures Agencourt GenFind kits for bead-based extraction chemistry. User Guides that describe in detail the protocol(s) to be followed are usually included in all these kits, for example, Qiagen's literature for their PureGene extraction chemistry entitled "Qiagen PureGene Handbook" 3rd Edition, dated June 2011.

After cells have been obtained from the sample, it is preferable to lyse cells in order to isolate genomic nucleic acid. Cellular extracts can be subjected to other steps to drive nucleic acid isolation toward completion by, e.g., differential precipitation, column chromatography, extraction with organic solvents and the like. Extracts then may be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. The genomic nucleic acid can also be resuspended in a hydrating solution, such as an aqueous buffer. The genomic nucleic acid can be suspended in, for example, water, Tris buffers, or other buffers. In certain embodiments the genomic nucleic acid can be re-suspended in Qiagen DNA hydration solution, or other Tris-based buffer of a pH of around 7.5.

Depending on the type of method used for extraction, the genomic nucleic acid obtained can vary in size. The integrity and size of genomic nucleic acid can be determined by pulse-field gel electrophoresis (PFGE) using an agarose gel.

In addition to genomic nucleic acids, whole genome amplification product and partial genomic amplification products can be used in aspects of the invention. Methods of obtaining whole genome amplification product and partial genome amplification product are described in detail in Pinter et al. U.S. Patent Publication Number 2004/0209299, and include, for example, generally ligation mediated PCR™, random primed PCR™, strand displacement mediated PCR™, and cell immortalization.

In certain embodiments, a genomic sample is collected from a subject followed by enrichment for genes or gene fragments of interest, for example by hybridization to a nucleotide array. The sample may be enriched for genes of interest using methods known in the art, such as hybrid capture. See for examples, Lapidus (U.S. Pat. No. 7,666,593), the content of which is incorporated by reference herein in its entirety. As will be described in more detail below, a preferable capture method uses molecular inversion probes.

Fragmenting the Nucleic Acid

Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993. Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. In one embodiment, the genomic nucleic acid fragments can range from 1 kilobases to 20 kilobases. Fragments can vary in size and have an average fragment length of about 10 kilobases. However, desired fragment length and ranges of fragment lengths can be adjusted depending on the type of nucleic acid targets one seeks to capture and the design and type of MIP probes. The particular method of fragmenting is selected to achieve the desired fragment length. Numerous non-limiting examples are provided below.

Chemical fragmentation of genomic nucleic acids can be achieved using a number of different methods. For example, hydrolysis reactions including base and acid hydrolysis are common techniques used to fragment nucleic acid. Hydrolysis is facilitated by temperature increases, depending upon the desired extent of hydrolysis. Fragmentation can be accomplished by altering temperature and pH as described below. The benefit of pH-based hydrolysis for shearing is that it can result in single-stranded products. Additionally, temperature can be used with certain buffer systems (e.g. Tris) to temporarily shift the pH up or down from neutral to accomplish the hydrolysis, then back to neutral for long-term storage etc. Both pH and temperature can be modulated to effect differing amounts of shearing (and therefore varying length distributions).

In one aspect, a nucleic acid is fragmented by heating a nucleic acid immersed in a buffer system at a certain temperature for a certain period to time to initiate hydrolysis and thus fragment the nucleic acid. The pH of the buffer system, duration of heating, and temperature can be varied to achieve a desired fragmentation of the nucleic acid. In one embodiment, after a genomic nucleic acid is purified, it is resuspended in a Tris-based buffer at a pH between 7.5 and 8.0, such as Qiagen's DNA hydrating solution. The resuspended genomic nucleic acid is then heated to 65° C. and incubated overnight (about 16-24 hours) at 65° C. Heating shifts the pH of the buffer into the low- to mid-6 range, which leads to acid hydrolysis. Over time, the acid hydrolysis causes the genomic nucleic acid to fragment into single-stranded and/or double-stranded products.

Other methods of hydrolytic fragmenting of nucleic acids include alkaline hydrolysis, formalin fixation, hydrolysis by metal complexes (e.g., porphyrins), and/or hydrolysis by hydroxyl radicals. RNA shears under alkaline conditions, see, e.g. Nordhoff et al., Nucl. Acid. Res., 21 (15):3347-57 (2003), whereas DNA can be sheared in the presence of strong acids or strong bases.

An exemplary acid/base hydrolysis protocol for producing genomic nucleic acid fragments is described in Sargent et al. (1988) Methods Enzymol., 152:432. Briefly, 1 g of purified DNA is dissolved in 50 mL 0.1 N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH ([OH-] concentration to 0.1 N) is added, and the sample is stirred until the DNA redissolves completely. The sample is then incubated at 65° C. for 30 minutes in order to hydrolyze the DNA. Resulting fragments typically range from about 250-1000 nucleotides but can vary lower or higher depending on the conditions of hydrolysis.

Chemical cleavage can also be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," J. Am. Chem. Soc. 124(27):7950-7962 (2002)). Alkylation at the phosphorothioate modification renders the nucleic acid molecule susceptible to cleavage at the modification site. See I. G. Gut and S. Beck, "A procedure for selective DNA alkylation and detection by mass spectrometry," Nucl. Acids Res. 23(8): 1367-1373 (1995).

Methods of the invention also contemplate chemically shearing nucleic acids using the technique disclosed in Maxam-Gilbert Sequencing Method (Chemical or Cleavage Method), Proc. Natl. Acad. Sci. USA. 74:560-564. In that protocol, the genomic nucleic acid can be chemically cleaved by exposure to chemicals designed to fragment the nucleic acid at specific bases, such as preferential cleaving at guanine, at adenine, at cytosine and thymine, and at cytosine alone.

Mechanical shearing of nucleic acids into fragments can occur using any method known in the art. For example, fragmenting nucleic acids can be accomplished by hydroshearing, trituration through a needle, and sonication. See, for example, Quail, et al. (November 2010) DNA: Mechanical Breakage. In: eLS. John Wiley & Sons, Chichester. doi: 10.1002/9780470015902.a0005 333.pub2.

The nucleic acid can also be sheared via nebulization, see (Roe, B A, Crabtree. J S and Khan, A S 1996); Sambrook & Russell, Cold Spring Harb Protoc 2006. Nebulizing involves collecting fragmented DNA from a mist created by forcing a nucleic acid solution through a small hole in a nebulizer. The size of the fragments obtained by nebulization is determined chiefly by the speed at which the DNA solution passes through the hole, altering the pressure of the gas blowing through the nebulizer, the viscosity of the solution, and the temperature. The resulting DNA fragments are distributed over a narrow range of sizes (700-1330 bp). Shearing of nucleic acids can be accomplished by passing obtained nucleic acids through the narrow capillary or orifice (Oefner et al., Nucleic Acids Res. 1996; Thorstenson et al., Genome Res. 1995). This technique is based on point-sink hydrodynamics that result when a nucleic acid sample is forced through a small hole by a syringe pump.

In HydroShearing (Genomic Solutions. Ann Arbor, Mich., USA). DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes.

Sonication is also used to fragment nucleic acids by subjecting the nucleic acid to brief periods of sonication, i.e. ultrasound energy. A method of shearing nucleic acids into fragments by sonification is described in U.S. Patent Publication 2009/0233814. In the method, a purified nucleic acid is obtained placed in a suspension having particles disposed within. The suspension of the sample and the particles are then sonicated into nucleic acid fragments.

An acoustic-based system that can be used to fragment DNA is described in U.S. Pat. Nos. 6,719,449, and 6,948,843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA.

Another method of shearing nucleic acids into fragments uses ultrasound energy to produce gaseous cavitation in liquids, such as shearing with Diagonnode's BioRuptor®. Cavitation is the formation of small bubbles of dissolved gases or vapors due to the alteration of pressure in liquids. These bubbles are capable of resonance vibration and produce vigorous eddying or microstreaming. The resulting mechanical stress can lead to shearing the nucleic acid in to fragments.

Enzymatic fragmenting, also known as enzymatic cleavage, cuts nucleic acids into fragments using enzymes, such as endonucleases, exonucleases, ribozymes, and DNAzymes. Such enzymes are widely known and are available commercially, see Sambrook, J. Molecular Cloning: A Laboratory Manual, 3rd (2001) and Roberts R J (January 1980). "Restriction and modification enzymes and their recognition sequences," Nucleic Acids Res. 8 (1): r63-r80. Varying enzymatic fragmenting techniques are well-known in the art, and such techniques are frequently used to fragment a nucleic acid for sequencing, for example, Alazard et al, 2002; Bentzley et al, 1998; Bentzley et al, 1996; Faulstich et al, 1997; Glover et al, 1995; Kirpekar et al, 1994; Owens et al, 1998; Pieles et al, 1993; Schuette et al, 1995; Smirnov et al, 1996; Wu & Aboleneen, 2001; Wu et al, 1998a.

The most common enzymes used to fragment nucleic acids are endonucleases. The endonucleases can be specific for either a double-stranded or a single stranded nucleic acid molecule. The cleavage of the nucleic acid molecule can occur randomly within the nucleic acid molecule or can cleave at specific sequences of the nucleic acid molecule. Specific fragmentation of the nucleic acid molecule can be accomplished using one or more enzymes in sequential reactions or contemporaneously.

Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II II, and IV) based on their composition and enzyme cofactor requirements, the nature of their target sequence, and the position of their DNA cleavage site relative to the target sequence. Bickle T A, Krüger D H (June 1993). "Biology of DNA restriction". Microbiol. Rev. 57 (2): 434-50; Boyer H W (1971). "DNA restriction and modification mechanisms in bacteria". Annu. Rev. Microbiol. 25: 153-76; Yuan R (1981). "Structure and mechanism of multifunctional restriction endonucleases". Annu. Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams R J (2003). "Restriction endonucleases: classification, properties, and applications". Mol. Biotechnol. 23 (3): 225-43.

Where restriction endonucleases recognize specific sequencings in double-stranded nucleic acids and generally cleave both strands, nicking endonucleases are capable of cleaving only one of the strands of the nucleic acid into a fragment. Nicking enzymes used to fragment nucleic acids can be naturally occurring or genetically engineered from restriction enzymes. See Chan et al., Nucl. Acids Res. (2011) 39 (1): 1-18.

Denaturing the Nucleic Acids

Methods of the invention also provide for denaturing nucleic acid to render the nucleic acid single stranded for hybridization to a capture probe, such as a MIP probe. Denaturation can result from the fragmentation method chosen, as described above. For example, one skilled in the art recognizes that a genomic nucleic acid can be denatured during pH-based shearing or fragmenting via nicking endonucleases. Denaturation can occur either before, during, or after fragmentation. In addition, the use of pH or heat during the fragmenting step can result in denatured nucleic acid fragments. See, for example, McDonnell, "Antisepsis, disinfection, and sterilization: types, action, and resistance," pg. 239 (2007).

Heat-based denaturing is the process by which double-stranded deoxyribonucleic acid unwinds and separates into single-stranded strands through the breaking of hydrogen bonding between the bases. Heat denaturation of a nucleic acid of an unknown sequence typically uses a temperature high enough to ensure denaturation of even nucleic acids having a very high GC content. e.g., 95° C.-98° C. in the absence of any chemical denaturant. It is well within the abilities of one of ordinary skill in the art to optimize the conditions (e.g., time, temperature, etc.) for denaturation of the nucleic acid. Temperatures significantly lower than 95° C. can also be used if the DNA contains nicks (and therefore sticky overhangs of low Tm) or sequence of sufficiently low Tm.

Denaturing nucleic acids with the use of pH is also well known in the art, and such denaturation can be accomplished using any method known in the art such as introducing a nucleic acid to high or low pH, low ionic strength, and/or heat, which disrupts base-pairing causing a double-stranded helix to dissociate into single strands. For methods of pH-based denaturation see, for example, Dore et al. Biophys J. 1969 November: 9(11): 1281-1311; A. M. Michelson The Chemistry of Nucleosides and Nucleotides, Academic Press, London and New York (1963).

Nucleic acids can also be denatured via electro-chemical means, for example, by applying a voltage to a nucleic acid within a solution by means of an electrode. Varying methods of denaturing by applying a voltage are discussed in detail in U.S. Pat. Nos. 6,197,508 and 5,993,611.

Molecular Inversion Probe Capture

Molecular inversion probe technology is used to detect or amplify particular nucleic acid sequences in complex mixtures. Use of molecular inversion probes has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). One of the main benefits of the method is in its capacity for a high degree of multiplexing, because generally thousands of targets may be captured in a single reaction containing thousands of probes.

In certain embodiments, molecular inversion probes include a universal portion flanked by two unique targeting arms. The targeting arms are designed to hybridize immediately upstream and downstream of a specific target sequence located on a genomic nucleic acid fragment. The molecular inversion probes are introduced to nucleic acid fragments to perform capture of target sequences located on the fragments. According to the invention, fragmenting aids in capture of target nucleic acid by molecular inversion probes. As described in greater detail herein, after capture of the target sequence (e.g., locus) of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filing incubation periods. (See, e.g., Turner E H, et al., Nat Methods. 2009 Apr. 6:1-2.).

In one embodiment of the present invention, a library of molecular inversion probes is generated, wherein the probes are used in capturing DNA of genomic regions of interests (e.g., SMN1, SMN2, control DNA). The library consists of a plurality of SMA oligonucleotide probes capable of capturing one or more genomic regions of interest (e.g., SMN1, SMN2 and control loci) within the samples to be tested.

The result of MIP capture as described above is a library of circular target probes, which then can be processed in a variety of ways. In one aspect, adaptors for sequencing can be attached during common linker-mediated PCR, resulting in a library with non-random, fixed starting points for sequencing. In another aspect, for preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production.

It should be appreciated that aspects of the invention can involve varying the amounts of genomic nucleic acid and varying the amounts of MIP probes to reach a customized result. In some embodiments, the amount of genomic nucleic acid used per subject ranges from 1 ng to 10 μg (e.g., 500 ng to 5 μg). However, higher or lower amounts (e.g., less than 1 ng, more than 10 μg, 10-50 μg, 50-100 μg or more) may be used. In some embodiments, for each locus of interest, the amount of probe used per assay may be optimized for a particular application. In some embodiments, the ratio (molar ratio, for example measured as a concentration ratio) of probe to genome equivalent (e.g., haploid or diploid genome equivalent, for example for each allele or for both alleles of a nucleic acid target or locus of interest) ranges from 1/100, 1/10, 1/1, 10/1, 100/1, 1000/1. However, lower, higher, or intermediate ratios may be used.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Similarly, once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

In some embodiments, it should be appreciated that one or more intervening sequences (e.g., sequence between the first and second targeting arms on a MIP capture probe), identifier or tag sequences, or other probe sequences that are not designed to hybridize to a target sequence (e.g., a genomic target sequence) should be designed to avoid excessive complementarity (to avoid cross-hybridization) to target sequences or other sequences (e.g., other genomic sequences) that may be in a biological sample. For example, these sequences may be designed to have a sufficient number of mismatches with any genomic sequence (e.g., at least 5, 10, 15, or more mismatches out of 30 bases) or to have a Tm (e.g., a mismatch Tm) that is lower (e.g., at least 5, 10, 15, 20, or more degrees C. lower) than the hybridization reaction temperature.

It should be appreciated that a targeting arm as used herein may be designed to hybridize (e.g., be complementary) to either strand of a genetic locus of interest if the nucleic acid being analyzed is DNA (e.g., genomic DNA). However, in the context of MIP probes, whichever strand is selected for one targeting arm will be used for the other one. However, in the context of RNA analysis, it should be appreciated that a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

It should be appreciated that in some embodiments a targeting arm may include a sequence that is complementary to one allele or mutation (e.g., a SNP or other polymorphism, a mutation, etc.) so that the probe will preferentially hybridize (and capture) target nucleic acids having that allele or mutation. However, in many embodiments, each targeting arm is designed to hybridize (e.g., be complementary) to a sequence that is not polymorphic in the subjects of a population that is being evaluated. This allows target sequences to be captured and/or sequenced for all alleles and then the differences between subjects (e.g., calls of heterozygous or homozygous for one or more loci) can be based on the sequence information and/or the frequency as described herein.

It should be appreciated that sequence tags (also referred to as barcodes) may be designed to be unique in that they do not appear at other positions within a probe or a family of probes and they also do not appear within the sequences being targeted. Thus they can be used to uniquely identify (e.g., by sequencing or hybridization properties) particular probes having other characteristics (e.g., for particular subjects and/or for particular loci).

It also should be appreciated that in some embodiments probes or regions of probes or other nucleic acids are described herein as including certain sequences or sequence characteristics (e.g., length, other properties, etc.). In addition, components (e.g., arms, central regions, tags, primer sites, etc., or any combination thereof) of such probes can include certain sequences or sequence characteristics that consist of one or more characteristics (e.g., length or other properties, ect.).

As disclosed herein, uniformity and reproducibility can be increased by designing multiple probes per target, such that each base in the target is captured by more than one probe. In some embodiments, the disclosure provides multiple MIPs per target to be captured, where each MIP in a set designed for a given target nucleic acid has a central region and a 5' region and 3' region ('targeting arms') which hybridize to (at least partially) different nucleic acids in the target nucleic acid (immediately flanking a subregion of the target nucleic acid). Thus, differences in efficiency between different targeting arms and fill-in sequences may be averaged across multiple MIPs for a single target, which results in more uniform and reproducible capture efficiency.

In some embodiments, the methods involve designing a single probe for each target (a target can be as small as a single base or as large as a kilobase or more of contiguous sequence).

It may be preferable, in some cases, to design probes to capture molecules (e.g., target nucleic acids or subregions thereof) having lengths in the range of 1-200 bp (as used herein, a bp refers to a base pair on a double-stranded nucleic acid—however, where lengths are indicated in bps, it should be appreciated that single-stranded nucleic acids having the same number of bases, as opposed to base pairs, in length also are contemplated by the invention). However, probe design is not so limited. For example, probes can be designed to capture targets having lengths in the range of up to 10, 20, 30, 40, 50, 60, 70, 80, 90, 100, 200, 300, 400, 500, 1000, or more bps, in some cases.

It is to be appreciated that the length of a capture molecule on a nucleic acid fragment (e.g., a target nucleic acid or subregion thereof) is selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

It is also to be appreciated that some target nucleic acids on a nucleic acid fragment are too large to be captured with one probe. Consequently, it may be necessary to capture multiple subregions of a target nucleic acid in order to analyze the full target.

In some embodiments, a sub-region of a target nucleic acid is at least 1 bp. In other embodiments, a subregion of a target nucleic acid is at least 10, 20, 30, 40, 50, 60, 70, 80, 90, 100, 200, 300, 400, 500, 600, 700, 800, 900, 1000 bp or more. In other embodiments, a subregion of a target nucleic acid has a length that is up to 10%, 20%, 30%, 40%, 50%, 60%, 70%, 80%, 90%, 95%, or more percent of a target nucleic acid length.

The skilled artisan will also appreciate that consideration is made, in the design of MIPs, for the relationship between probe length and target length. In some embodiments, MIPs are designed such that they are several hundred basepairs (e.g., up to 100, 200, 300, 400, 500, 600, 700, 800, 900, 1000 bp or more) longer than corresponding target (e.g., subregion of a target nucleic acid, target nucleic acid). In some embodiments, lengths of subregions of a target nucleic acid may differ.

For example, if a target nucleic acid contains regions for which probe hybridization is not possible or inefficient, it may be necessary to use probes that capture subregions of one or more different lengths in order to avoid hybridization with problematic nucleic acids and capture nucleic acids that encompass a complete target nucleic acid.

Methods of the invention also provide for combining the method of fragmenting the nucleic acid prior to capture with other MIP capture techniques that are designed to increase target uniformity, reproducibility, and specificity. Other MIP capture techniques are shown in co-owned and pending application, U.S. patent application Ser. No. 13/266,862, "Methods and Compositions for Evaluating Genetic Markers."

For example, multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence). Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted by changing the number of different MIPs used to capture a given molecule.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Barcode PCR

With these methods, a single copy of a specific target nucleic acid may be amplified to a level that can be sequenced. Further, the amplified segments created by an amplification process such as PCR may be, themselves, efficient templates for subsequent PCR amplifications.

Amplification or sequencing adapters or barcodes, or a combination thereof, may be attached to the fragmented nucleic acid. Such molecules may be commercially obtained, such as from Integrated DNA Technologies (Coralville, IA). In certain embodiments, such sequences are attached to the template nucleic acid molecule with an enzyme such as a ligase. Suitable ligases include T4 DNA ligase and T4 RNA ligase, available commercially from New England Biolabs (Ipswich, MA). The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, WI). Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain embodiments, one or more bar code is attached to each, any, or all of the fragments. A bar code sequence generally includes certain features that make the sequence useful in sequencing reactions. The bar code sequences are designed such that each sequence is correlated to a particular portion of nucleic acid, allowing sequence reads to be correlated back to the portion from which they came. Methods of designing sets of bar code sequences is shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. In certain embodiments, the bar code sequences are attached to the template nucleic acid molecule, e.g., with an enzyme. The enzyme may be a ligase or a polymerase, as discussed above. Attaching bar code sequences to nucleic acid templates is shown in U.S. Pub. 2008/0081330 and U.S. Pub. 2011/0301042, the content of each of which is incorporated by reference herein in its entirety. Methods for designing sets of bar code sequences and other methods for attaching bar code sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety. After any processing steps (e.g., obtaining, isolating, fragmenting, amplification, or barcoding), nucleic acid can be sequenced.

Sequencing

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

A sequencing technique that can be used includes, for example, Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Sequencing generates a plurality of reads. Reads generally include sequences of nucleotide data less than about 150 bases in length, or less than about 90 bases in length. In certain embodiments, reads are between about 80 and about 90 bases, e.g., about 85 bases in length. In some embodiments, these are very short reads, i.e., less than about 50 or about 30 bases in length.

Data Analysis

The sequence reads are analyzed to determine copy number states of genomic regions of interest. A set of sequence reads can be analyzed by any suitable method known in the art. For example, in some embodiments, sequence reads are analyzed by hardware or software provided as part of a sequence instrument. In some embodiments, individual sequence reads are reviewed by sight (e.g., on a computer monitor). A computer program may be written that pulls an observed genotype from individual reads. In certain embodiments, analyzing the reads includes assembling the sequence reads and then genotyping the assembled reads.

Sequence assembly can be done by methods known in the art including reference-based assemblies, de novo assemblies, assembly by alignment, or combination methods. Assembly can include methods described in U.S. Pat. No. 8,209,130 titled Sequence Assembly by Porecca and Kennedy, the contents of each of which are hereby incorporated by reference in their entirety for all purposes. In some embodiments, sequence assembly uses the low coverage sequence assembly software (LOCAS) tool described by Klein, et al., in LOCAS-A low coverage sequence assembly tool for re-sequencing projects, PLoS One 6(8) article 23455 (2011), the contents of which are hereby incorporated by reference in their entirety. Sequence assembly is described in U.S. Pat. Nos. 8,165,821; 7,809,509; 6,223,128; U.S. Pub. 2011/0257889; and U.S. Pub. 2009/0318310, the contents of each of which are hereby incorporated by reference in their entirety.

As part of the analysis and determination of copy number states and subsequent identification of copy number variation, the sequence read counts for genomic regions of interest are normalized based on internal controls. In particular, an intra-sample normalization is performed to control for variable sequencing depths between samples. The sequence read counts for each genomic region of interest within a sample will be normalized according to the total mad count across all control references within the sample.

After normalizing read counts for both the genomic regions of interest and control references, copy number states may be determined. In one embodiment, the normalized values for each sample of interest will be compared to the normalized values for a control sample. A ratio, for example, may be generated based on the comparison, wherein the ratio is indicative of copy number and further determinative of any copy number variation. In the event that the determined copy number of a genomic region of interest of a particular sample falls within a tolerable level (as determined by ratio between test and control samples), it can be determined that genomic region of interest does not present copy number variation and thus the patient is at low risk for being a carrier of a condition or disease associated with such. In the event that the determined copy number of a genomic region of interest of a particular sample falls outside of a tolerable level, it can be determined that genomic region of interest does present copy number variation and thus the patient is at risk for being a carrier of a condition or disease associated with such.

Example

Determination of Copy Number State of SMN1

The following example shows a preferred method of practicing the invention.

A total of approximately 28 samples were collected from a patient to determine carrier status with respect to spinal muscular atrophy (SMA). In one embodiment, genomic DNA was extracted from whole human blood using a Gentra Puregene Blood Kit and following the Puregene protocol for DNA Purification from Whole Blood (Qiagen). The protocol can be scaled (i.e. amount of solution, duration) to accommodate the desired amount of whole genomic DNA. The samples were collected via any methods previously described herein. Further, it should be noted that the DNA could be collected from other types of samples (e.g., tissue, mucous, etc.).

Of the 28 samples, there is 1 water negative control and 7 control DNA samples and 20 test samples. Each of the control samples includes two or more genomic regions of interest (e.g. loci) having known (or stable) copy numbers. The details of each control sample are included in Table 1 below:

TABLE 1

| Control Samples | | | |
| --- | --- | --- | --- |
| Control Sample ID | Locus | Number of Loci | Copy Number |
| Controls 1-4 (each) | Control | 17 | 2 |
| | SMN1 | 5 | 2 |
| | SMN2 | 5 | 2 |
| Control 5 | Control | 17 | 2 |
| | SMN1 | 5 | 0 |
| Control 6 | Control | 17 | 2 |
| | SMN1 | 5 | 1 |
| Control 7 | Control | 17 | 2 |
| | SMN1 | 5 | 3+ |

Control samples 1-4 each include control loci and survival motor neuron genes (SMN), including telomeric SMN (SMN1) and centromeric SMN (SMN2) genes. There are a total of 17 control loci, 5 SMN1, and 5 SMN2, all of which have a known copy number of 2. Control sample 5 includes 17 control loci, each having a known copy number of 2, and 5 SMN1, each having a known copy number of 0. Control sample 6 includes 17 control loci, each having a known copy number of 2, and 5 SMN1, each having a known copy number of 1. Control sample 7 includes 17 control loci, each having a known copy number of 2, and 5 SMN1, each having a known copy number of 3 or more. As described in greater detail herein, inclusion of the control samples into the overall sample size allows identification of copy number states and any copy number variation of SMN1 and/or SMN2 captured from the test samples, thereby allowing subsequent determination of carrier status of a patient based on the copy number variation.

Each sample was first normalized by any know normalizing techniques. The normalized samples were then fragmented and/or denatured in preparation for hybridizing with molecular inversion probes. The genomic DNA of each sample was fragmented/denatured by any known method or technique sufficient to fragment genomic DNA.

Once isolated, MIP capture probes were hybridized to isolated fragmented genomic DNA in each sample by introducing capture probe mix into each sample well. In particular, the capture probe mix will generally include a plurality of SMA molecular inversion probes that are capable of binding to one or more of the genomic regions of interest (e.g., SMN1 and SMN2) or the control DNA. A library of molecular inversion probes was generated. The library may include a variety of different probe configurations. For example, one or more probes are capable of hybridizing specifically to the control loci and one or more probes are capable of hybridizing only to SMN1 or SMN2. Of those probes specific to SMN1 or SMN2, some are capable of producing sequences specific to that paralog while some are not capable of producing paralog-specific sequences. It should be noted that some methods described herein may utilized only one of these options. The library may also include one or more probes capable of hybridizing nonspecifically to both SMN1 and SMN2. During the sequencing process, described in greater detail herein, the non-specificity may be resolved by reading out the sequence captured by the non-specific probe, wherein the sequence may generally be specific to either SMN1 or SMN2 (a variant present in the captured sequence that is specific for one or the other paralog).

Diluted probes were introduced to the isolated fragmented genomic DNA in each sample and the isolated whole genomic DNA was incubated in the diluted probe mix to promote hybridization. The time and temperature for incubation may be based on any known hybridization protocol, sufficient to result in hybridization of the probes to the DNA. After capture of the genomic region of interest (e.g., SMN1, SMN2) the captured region is subjected to an enzymatic gap-filling and ligation step, in accordance with any known methods or techniques, including those generally described herein. The captured material may further be purified.

The purified captured DNA is then amplified by any known amplification methods or techniques. In one embodiment, the purified captured DNA was amplified using barcode-based PCR, in accordance with methods previously described herein. The resulting barcodes PCRs for each sample are then combined into a master pool and quantified.

After PCR, portions of the PCR reactions for each sample were pooled and purified, then quantified. In particular, the PCR reactions for all samples were pooled in equal volumes into one master pool. The master sample pool was then purified via a PCR cleanup protocol according to manufacturer's instructions. For example, Qiagen QIAquick PCR cleanup kit (Qiagen) was used to purify the sample pool, in accordance with the manufacturer's instructions.

The purified pool was then run on a microfluidics-based platform for sizing, quantification and quality control of DNA, RNA, proteins and cells. In particular, the purified pool and control samples (pre-purification), were run on Agilent Bioanalyzer for the detection and quantification of CF probe products and SMA probe products.

Next, the sample pool is prepared for sequencing. In a preferred embodiment, Illumina sequencing techniques were used. Prior to sequencing, the sample pool was reduced to 2 nM by diluting with 1×TE. Template DNA for cluster generation was prepared by combining 10 uL of 0.1 N NaOH with 10 uL of 2 nM DNA library (sample pool) and incubating said mixture at room temperature for 5 min. The mixture was then mixed with 980 uL of HT1 buffer (Illumina), thereby reducing the denatured library to a concentration of 20 pM. This mixture was then mixed (e.g., inversion) and pulse centrifuged. Next, 225 uL of the 20 pM library was mixed with 775 uL of HT1 buffer to reduce the library pool to a concentration of 4.5 pM. The library pool having a concentration of 4.5 pM is used for on-board clustering in the sequencing described below.

The sequencing, and subsequent analysis, was carried out on the HiSeq 2500/1500 system sold by Illumina, Inc. (San Diego, CA). Sequencing was carried out with the TruSeq Rapid PE Cluster Kit and TruSeq Rapid SBS 200 cycle kit (Illumina) and in accordance with manufacturer's instructions. In addition to the reagents and mixes included within the kits, additional reagents were prepared for genomic read sequencing primers and reverse barcode sequencing primers.

The library pool undergoes sequencing under paired-end, dual-index run conditions. Sequencing generates a plurality of reads. Reads generally include sequences of nucleotide data less than about 150 bases in length, or less than about 90 bases in length. In certain embodiments, reads are between about 80 and about 90 bases, e.g., about 85 bases in length. In some embodiments, these are very short reads, i.e., less than about 50 or about 30 bases in length. After obtaining sequence reads, they are further processed as illustrated in FIG. 1.

FIG. 1 is a flow diagram illustrating one embodiment of a method for determining copy number state of one of more genomic regions of interest in a sample. The method 100 includes obtaining sequence reads (operation 102) and normalizing read counts (operation 104). As described in greater detail herein, read counts for a genomic region of interest are normalized with respect to an internal control DNA. The method 100 further includes comparing normalized read counts to the internal control DNA (operation 106), thereby obtaining a ratio. The method further includes determining a copy number state of the genomic region of interest (operation 108) based on the comparison, specifically the ratio.

The plurality of reads generated by the sequencing method described above are analyzed to determine copy number states, and ultimately copy number variation, in any of the genomic regions of interest (e.g., SMN1 and SMN2) that would necessarily indicate the presence of an autosomal recessive trait in which copy number variation is diagnostic (e.g., spinal muscular atrophy). Analysis of the read counts is carried out using Illumina's HiSeq BclConverter software. Files (e.g., qSeq files) may be generated for both the genomic and barcode reads. In particular, in accordance with one method of the present invention, genomic read data for each sample is split based upon the barcode reads, which yields separate FASTQ files for each sample.

Analysis of the sequence results has a first step of normalizing the read counts for the SMN1 and SMN2 loci (genetic regions of interest for SMA). The read counts are normalized by dividing the read counts with a read count sum for a control. The read count sum generally includes all 17 SMA control loci of the 7 control samples. Then, the average normalized values for a set of pre-determined or empirically-identified (e.g., by analysis iteration) wild-type control samples are obtained. Then the normalized read counts for each test sample (each locus) are compared to the normalized read counts for each of the control samples, thereby obtaining a ratio of normalized read count of test samples/normalized read count of controls.

Based on the ratios, loci copy numbers may be called as follows: a ratio of <0.1 will be called a copy number state of 0; a ratio between 0.1 and 0.8 will be called a copy number state of 1; a ratio between 0.8 and 1.25 will be called a copy number state of 2; and a ratio of >1.25 will be called a copy number state of 3+.

The determined copy numbers can then be used to determine the carrier status of an individual from which the sample was obtained (i.e. whether the patient is a carrier of the disease). In particular, if the copy number state is determined to vary from the normal copy state (e.g., CN is 0, 1 or 3+), it is indicative the condition (e.g., carrier of SMA).

Additionally, or alternatively, upon initial normalization of the read counts for the test samples and control samples, the resulting vector of normalized frequencies may include $x=[f1, f2, \ldots, fn]$ which correspond to the frequencies of each of the loci being queried (test and control). The normalized frequencies from either a single control sample or a "synthetic" control (average of multiple control samples) $y=[g1, g2, \ldots, gn]$ may be used to calculate the copy number of each locus interrogated $c=x./y=[f1/g1, f2/g2, \ldots, fn/gn]$.

Functions described above can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system 200 for implementing some or all of the described inventive methods can include one or more processors (e.g., a central processing unit (CPU) a graphics processing unit (GPU), or both), main memory and static memory, which communicate with each other via a bus.

Figure 2:
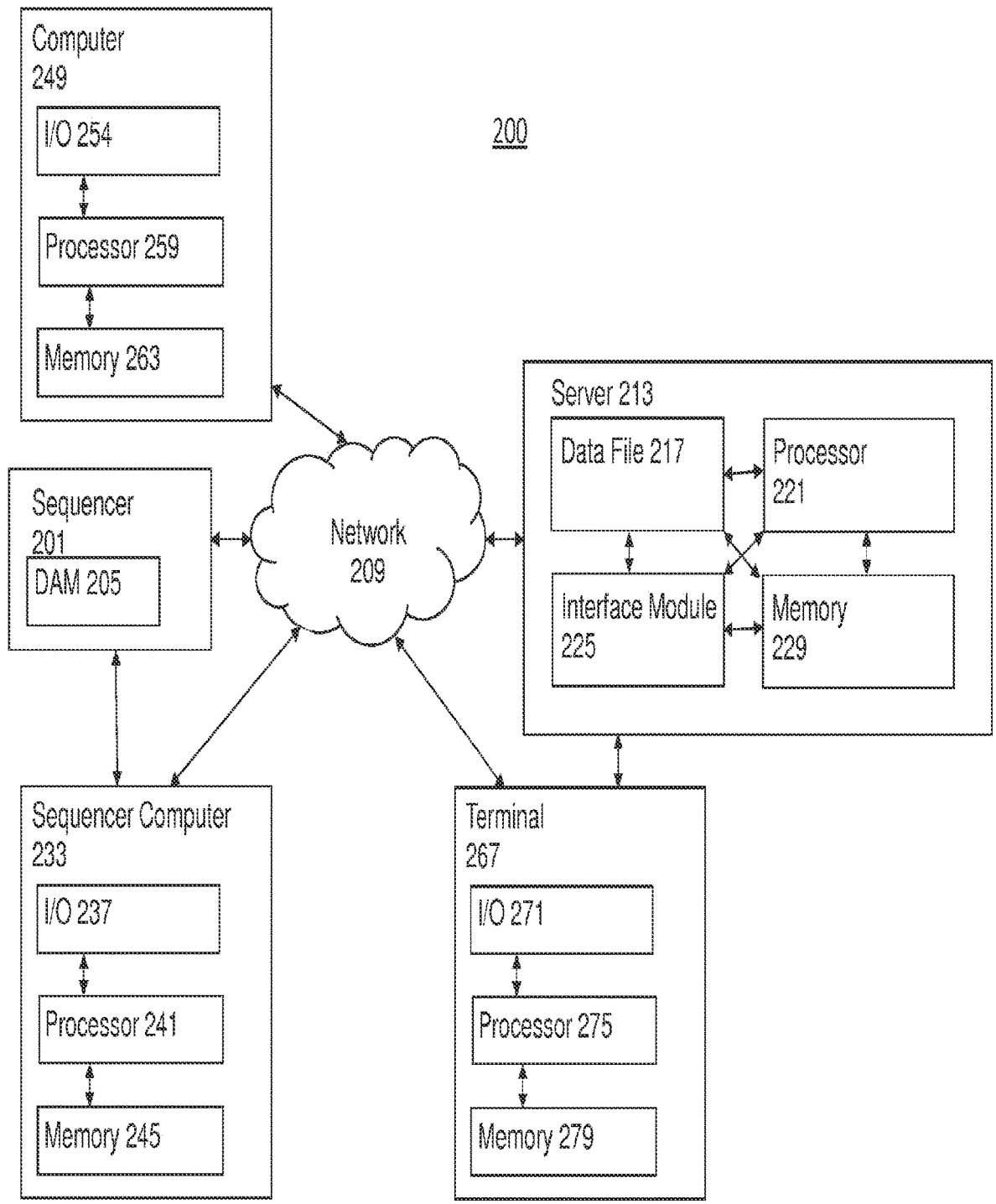
FIG. 2 illustrates a system for performing methods of the invention.

In an exemplary embodiment shown in FIG. 2, system 200 includes a sequencer 201 with a data acquisition module 205 to obtain sequence read data. The sequencer 201 may optionally include or be operably coupled to its own, e.g., dedicated, sequencer computer 233 (including an input/output mechanism 237, one or more of processor 241, and memory 245). Additionally or alternatively, the sequencer 201 may be operably coupled to a server 213 or computer 249 (e.g., laptop, desktop, or tablet) via a network 209. As previously described herein, the sequencer 201 may include the HiSeq 2500/1500 system sold by Illumina, Inc. (San Diego, CA).

The computer 249 includes one or more processors 259 and memory 263 as well as an input/output mechanism 254. Where methods of the invention employ a client/server architecture, steps of methods of the invention may be performed using the server 213, which includes one or more of processors 221 and memory 229, capable of obtaining data, instructions, etc., or providing results via an interface module 225 or providing results as a file 217. The server 213 may be engaged over the network 209 by the computer 249 or the terminal 267, or the server 213 may be directly connected to the terminal 267, which can include one or more processors 275 and memory 279, as well as an input/output mechanism 271.

The system or machines 200 according to the invention may further include, for any of I/O 249, 237, or 271, a video display unit (e.g., a liquid crystal display (LCD) or a cathode ray tube (CRT)). Computer systems or machines used to implement some or all of the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 245, 279, or 229 can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro SD card, or solid-state drive (SSD)), optical and magnetic media, and/or any other tangible storage medium or media.

The invention solves problems associated with current carrier screening assays by providing molecular inversion probes for capturing at least one genomic region known or suspected to be associated with a disease and subsequently sequencing the captured DNA to determine the copy number state of the captured DNA. In certain aspects, the captured DNA may be sequenced by known high-throughput sequence methods or techniques. The carrier status for the disease can then be determined based on the identified copy number state. In particular, the copy number state may be indicative of whether the patient is a carrier of a particular disease or condition for which copy number variation is diagnostic, such as an autosomal recessive trait (e.g., spinal muscular atrophy). For example, it can be determined whether copy number variation exists in the genomic regions of interest based on the identified copy number, thereby providing a method for determining whether the patient is a carrier of such an autosomal recessive trait.

Accordingly, the invention overcomes the problems of current carrier screening assays, particularly MLPA-based assays, based, at least in part, on compatibility with automated high-throughput screening. In particular, the invention provides the sensitivity and specificity for detection of copy number variation in SMN1 and/or SMN2, similar to MLPA-based methods, by utilizing molecular inversion probes. Additionally, by using high-throughput screening methods, the invention allows detection of deleterious SMN1 point mutations and indels that would otherwise be missed by MLPA and related approaches, thereby providing more reliable and accurate diagnosis.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for determination of copy number, the method comprising the steps of:
    exposing a sample to a plurality of molecular inversion probes (MIPs), wherein a first MIP hybridizes to a genomic region suspected of having an altered copy number and a second MIP hybridizes to an internal control DNA suspected of having a stable copy number;
    capturing, using the MIPs, the genomic region and the internal control DNA in said sample;
    sequencing said genomic region and the internal control DNA, thereby to obtain sequence reads;
    operating a computer system to
        provide read counts, of the sequence reads, for said genomic region and the internal control DNA;
        normalize said read counts for the genomic region with respect to the internal control DNA;
        compare normalized read counts for said genomic region with a standard; and
        infer copy number status of said genomic region based upon said comparing step.

2. The method of claim 1, wherein said genomic region is implicated in an autosomal recessive disorder.

3. The method of claim 2, wherein said genomic region is SMN1 or SMN2.

4. A method for determination of copy number, the method comprising the steps of:
    exposing a sample to a plurality of molecular inversion probes (MIPs) that include a first MIP capable of hybridizing to a locus in DNA from the sample and a second MIP capable of hybridizing to a control locus in the DNA;
    capturing, with said plurality of probes, the locus and the control locus;
    sequencing said the captured locus and the control locus to obtain sequence reads;

analyzing, by a computer system, the sequence reads to obtain read counts for the locus and the control locus;

normalizing said read counts for the locus with respect to the control locus, the copy number of which is stable;

comparing normalized read counts for the locus with a standard; and inferring copy number status of the locus based upon said comparing step.

5. The method of claim 1, wherein the computer system comprises a processor couple to a memory.

6. The method of claim 1, wherein the step of exposing a sample comprises obtaining a sample from a patient, the sample comprising genomic DNA that includes a genomic region suspected of having an altered copy number; and fragmenting the genomic DNA to yield target nucleic acid comprising fragments of the genomic region.

7. The method of claim 6, further comprising the step of diagnosing a carrier phenotype for spinal muscular atrophy.

8. The method of claim 1, wherein the sequencing step comprises a next-generation sequencing method.

9. The method of claim 1, further comprising determining a difference between the copy number status of the genomic region and a copy number distribution encompassing a plurality of stable control loci.

10. The method of claim 1, wherein the sample is blood.

11. The method of claim 4, wherein the computer system comprises a processor couple to a memory.

12. The method of claim 4, wherein the step of exposing a sample comprises obtaining a sample from a patient, the sample comprising genomic DNA that includes a genomic region suspected of having an altered copy number; and fragmenting the genomic DNA to yield target nucleic acid comprising fragments of the genomic region.

13. The method of claim 12, wherein the genomic region comprises a first gene and a second gene, wherein the first and second genes are homologs, orthologs, or paralogs.

14. The method of claim 12, further comprising the step of diagnosing a carrier phenotype for spinal muscular atrophy.

15. The method of claim 4, wherein the sequencing step comprises a next-generation sequencing method.

16. The method of claim 4, further comprising determining a difference between the copy number status of the locus and a copy number distribution encompassing a plurality of stable control loci.

17. The method of claim 4, wherein the sample is blood.

* * * * *